United States Patent
Fukunaga et al.

(10) Patent No.: US 7,611,672 B1
(45) Date of Patent: Nov. 3, 2009

(54) MEASUREMENT CELL

(75) Inventors: Atsushi Fukunaga, Osaka (JP); Eiji Noguchi, Osaka (JP); Takahiro Nakaminami, Osaka (JP)

(73) Assignee: Panasonic Corporation, Osaka (JP)

( * ) Notice: Subject to any disclaimer, the term of this patent is extended or adjusted under 35 U.S.C. 154(b) by 37 days.

(21) Appl. No.: 12/092,212

(22) PCT Filed: Nov. 27, 2006

(86) PCT No.: PCT/JP2006/323547

§ 371 (c)(1),
(2), (4) Date: Apr. 30, 2008

(87) PCT Pub. No.: WO2007/063791

PCT Pub. Date: Jun. 7, 2007

(30) Foreign Application Priority Data

Nov. 29, 2005 (JP) ............................. 2005-344184

(51) Int. Cl.
*B01L 3/00* (2006.01)
*G01N 1/10* (2006.01)

(52) U.S. Cl. ...................... 422/102; 422/55; 422/73; 422/99; 356/246; 356/244

(58) Field of Classification Search ............... 422/102, 422/55, 73, 99; 356/246, 244
See application file for complete search history.

(56) References Cited

U.S. PATENT DOCUMENTS

| | | | | |
|---|---|---|---|---|
| 5,285,253 A | * | 2/1994 | Kloth | 356/246 |
| 6,249,345 B1 | * | 6/2001 | Kraack et al. | 356/246 |
| 7,138,091 B2 | * | 11/2006 | Lee et al. | 422/102 |

FOREIGN PATENT DOCUMENTS

| | | |
|---|---|---|
| JP | 63-138236 | 6/1988 |
| JP | 9-113440 | 5/1997 |
| JP | 10-273331 | 5/1997 |
| JP | 2005-140621 | 6/2005 |

* cited by examiner

*Primary Examiner*—Jill Warden
*Assistant Examiner*—Sally A Sakelaris
(74) *Attorney, Agent, or Firm*—McDermott Will & Emery LLP

(57) ABSTRACT

A measurement cell 1 includes: an opening part 106 for supplying a sample into a sample holding part 105 for holding a sample; an optical window portion for allowing light to enter the sample holding part 105 and allowing light to exit the sample holding part 105; a protection cover 101 for protecting the optical window portion, provided along the circumference of the sample holding part 105; and a first protection-cover-holding part 102 for holding the protection cover 101 at the position where the optical window portion is covered.

6 Claims, 22 Drawing Sheets

F I G. 3
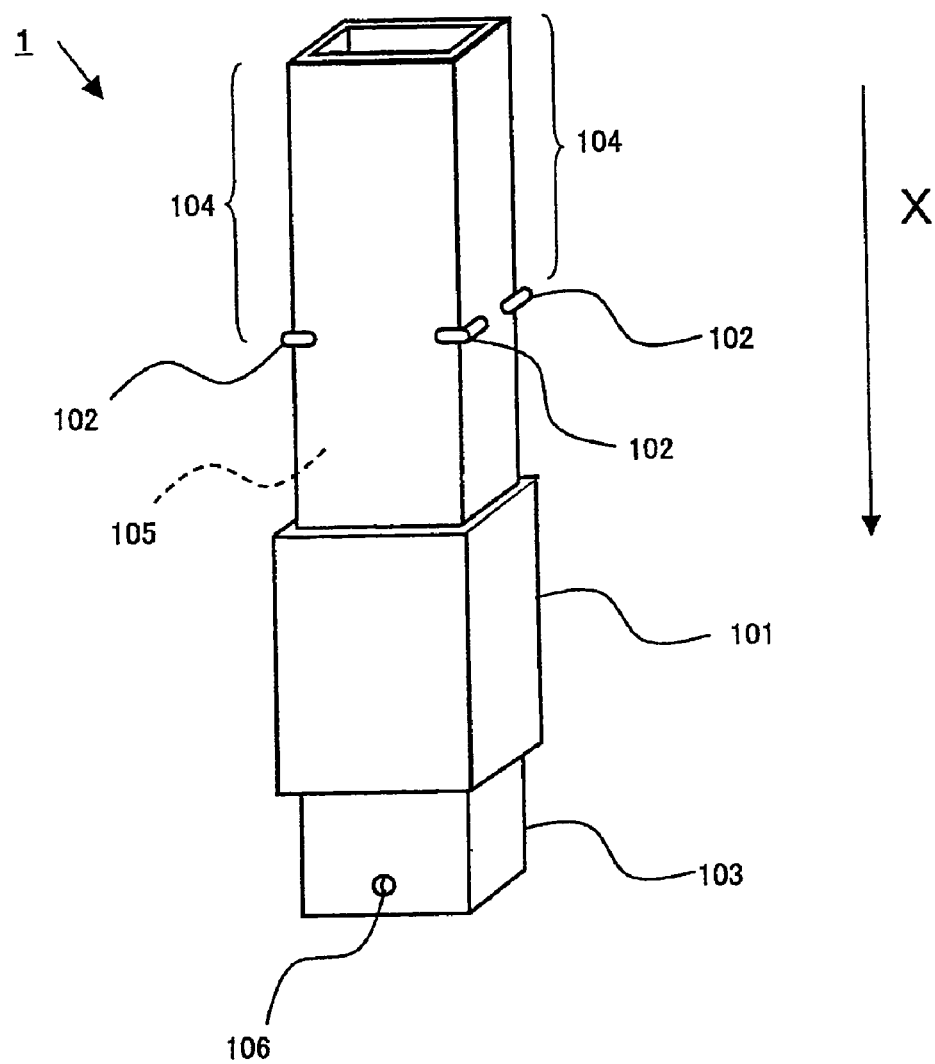

F I G. 5
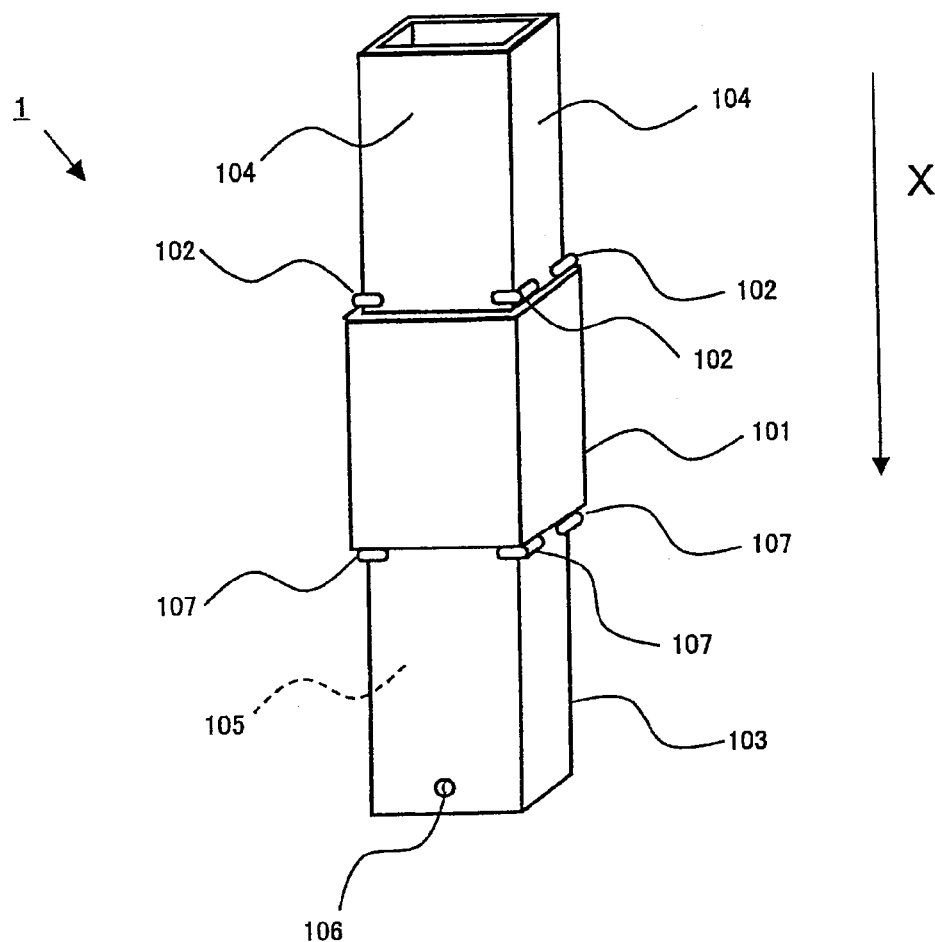

F I G. 1 2
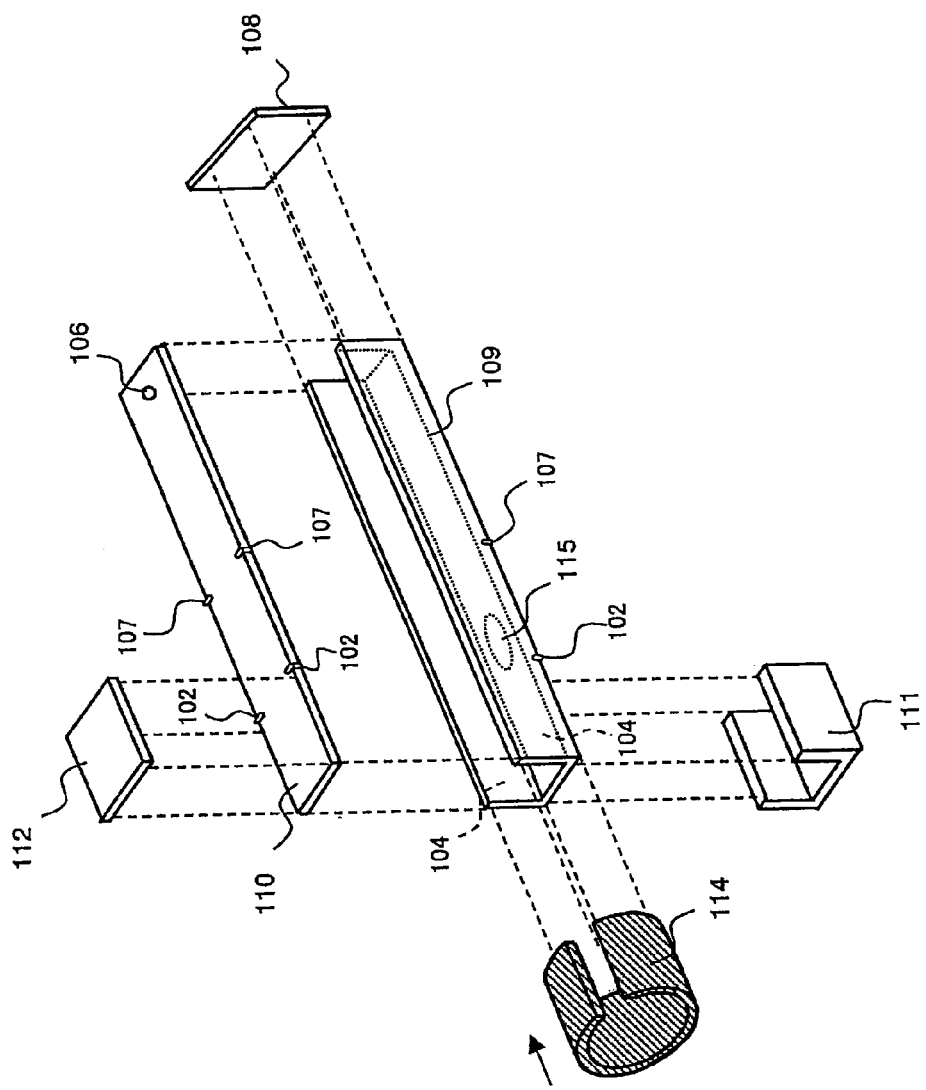

F I G. 1 8
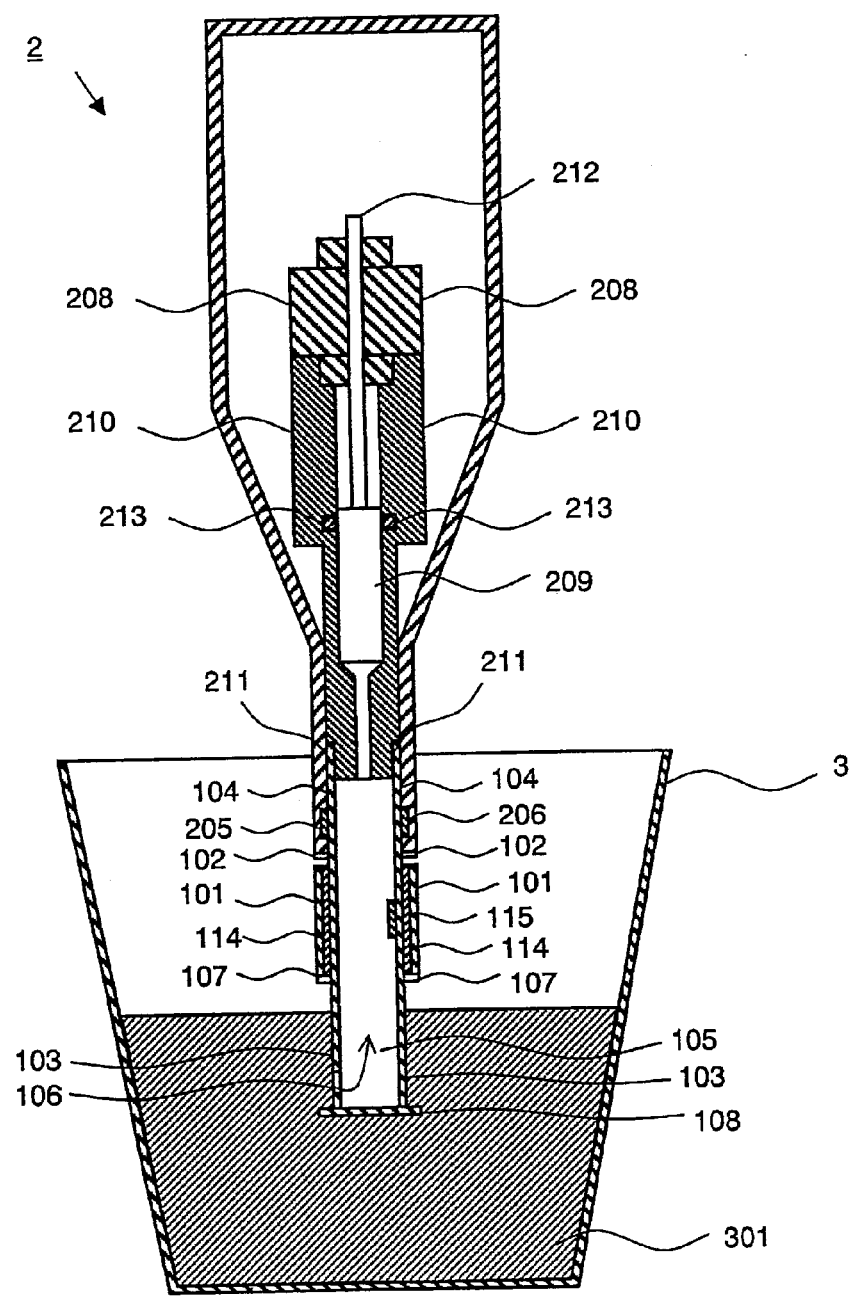

MEASUREMENT CELL

This application is the U.S. National Phase under 35 U.S.C. § 371 of International Application No. PCT/JP2006/323547, filed on Nov. 27, 2006, which in turn claims the benefit of Japanese Application No. 2005-344184, filed on Nov. 29, 2005, the disclosures of which. Applications are incorporated by reference herein.

TECHNICAL FIELD

The present invention relates to a measurement cell for optically measuring an analyte included in a sample.

BACKGROUND ART

So far, as a measurement cell used for an optical measurement on a sample, there has been proposed a prismatic glass cell configured to provide an optical window portion with a concave surface, for preventing the optical window portion positioned at the side face of the measurement cell from getting dirty or damaged (for example, Patent Document 1).

Patent Document 1 Japanese Laid-Open Patent Publication No. Hei 10-273331

DISCLOSURE OF THE INVENTION

Problem to be Solved by the Invention

However, there are some problems in the optical window portion of the cell described in the above patent document 1: the optical window portion is always exposed to the outside and the optical window portion cannot be protected sufficiently from dirt and damage, and such dirt and damage attached to the optical window portion cause error in measurement.

Thus, the present invention aims to provide a measurement cell capable of solving the conventional problems such as the one mentioned above, and of preventing measurement error due to dirt and damage by protecting the optical window portion.

Means for Solving the Problem

To solve the above problems, a measurement cell of the present invention is configured to include:

a sample holding part for holding a sample;

an opening part for supplying the sample to the inner portion of the sample holding part;

an optical window portion for allowing light to enter the sample holding part and allowing light to exit the sample holding part;

a protection cover for protecting the optical window portion, provided movably along the circumference of the sample holding part; and a first protection-cover-holding part for holding the protection cover at a position where the optical window portion is covered with the protection cover.

Based on such a configuration, not only the optical window portion can be protected by the protection cover, but also error in measurement due to dirt and damage on the optical window portion can be prevented further reliably by moving the protection cover to the position where the optical window portion is exposed upon measurement.

EFFECT OF THE INVENTION

Based on the measurement cell of the present invention, the optical window portion can be protected without being exposed when not in measurement, and the measurement error due to dirt and damage on optical window portion can be prevented further reliably.

BRIEF DESCRIPTION OF THE DRAWINGS

FIG. 3 A perspective view illustrating the measurement cell 1 shown in FIG. 1 with the protection cover 101 moved.

FIG. 5 A perspective view illustrating the measurement cell 1 shown in FIG. 4 with the protection cover 101 moved.

FIG. 12 An exploded perspective view of the measurement cell 1 in Embodiment 4.

FIG. 18 A diagram for describing still another step in the steps for measuring an analyte in a sample by using a measurement cell 1 and a measurement device 2 of the present invention.

BEST MODE FOR CARRYING OUT THE INVENTION

Figure 1:
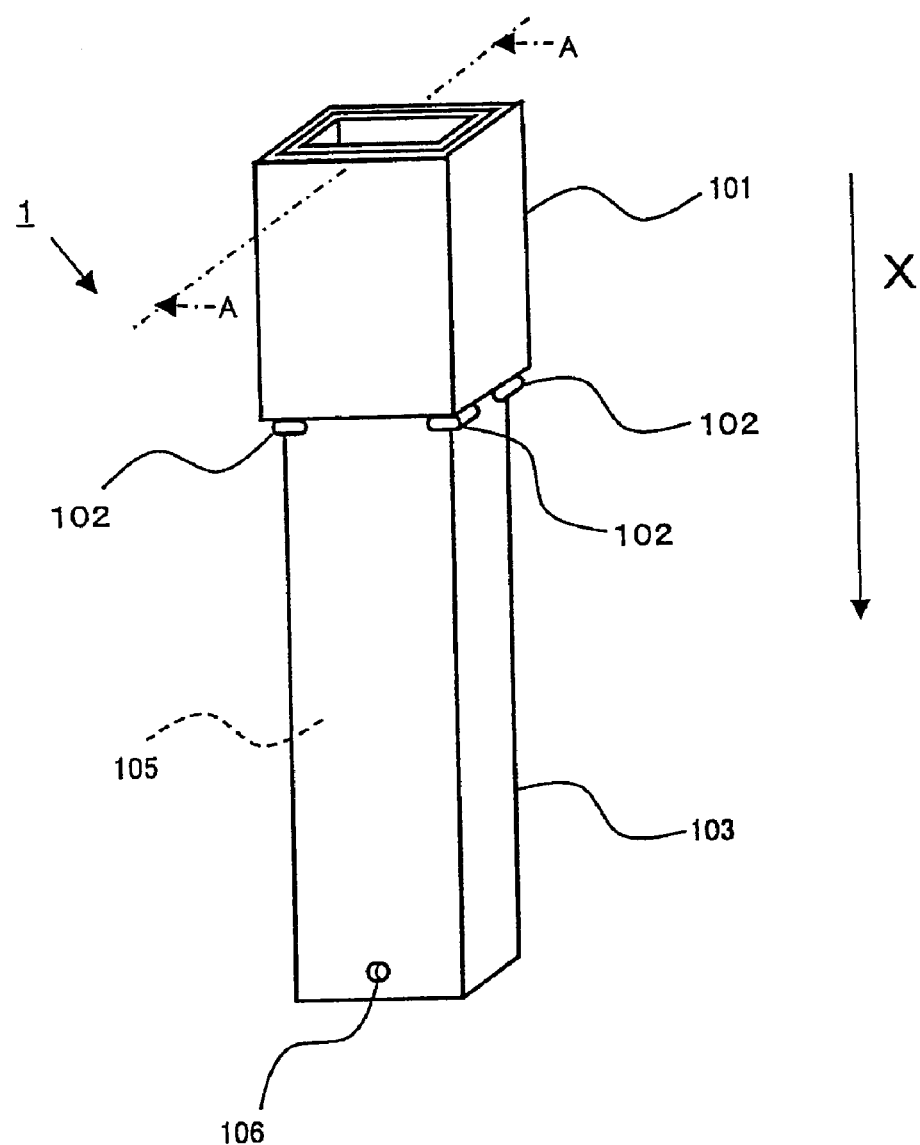
FIG. 1 A perspective view illustrating a configuration of a measurement cell in Embodiment 1 of the present invention.

The measurement cell of the present invention is characterized in that a protection cover for protecting an optical window portion is provided.

That is, the measurement cell of the present invention comprises:

a sample holding part for holding a sample;

an opening part for supplying the sample to the inner portion of the sample holding part;

an optical window portion for allowing light to enter the sample holding part and allowing light to exit the sample holding part;

a protection cover for protecting the optical window portion, provided movably along the circumference of the sample holding part; and a first protection-cover-holding part for holding the protection cover at a position where the optical window portion is covered with the protection cover.

The measurement cell of the present invention may further include a second protection-cover-holding part for holding the protection cover at a position where the optical window portion and the opening part are exposed.

The measurement cell of the present invention may further include a third protection-cover-holding part for holding the protection cover at a position where the opening part is covered.

In the measurement cell of the present invention, an absorbent may be provided at the inner side of the protection cover.

In the following, preferable embodiments of the measurement cell of the present invention are described in detail by referring to FIGS. In the following description, the same reference numerals are used for the same or corresponding part, and redundant description may be omitted.

Embodiment 1

1. Measurement Cell

Figure 2:
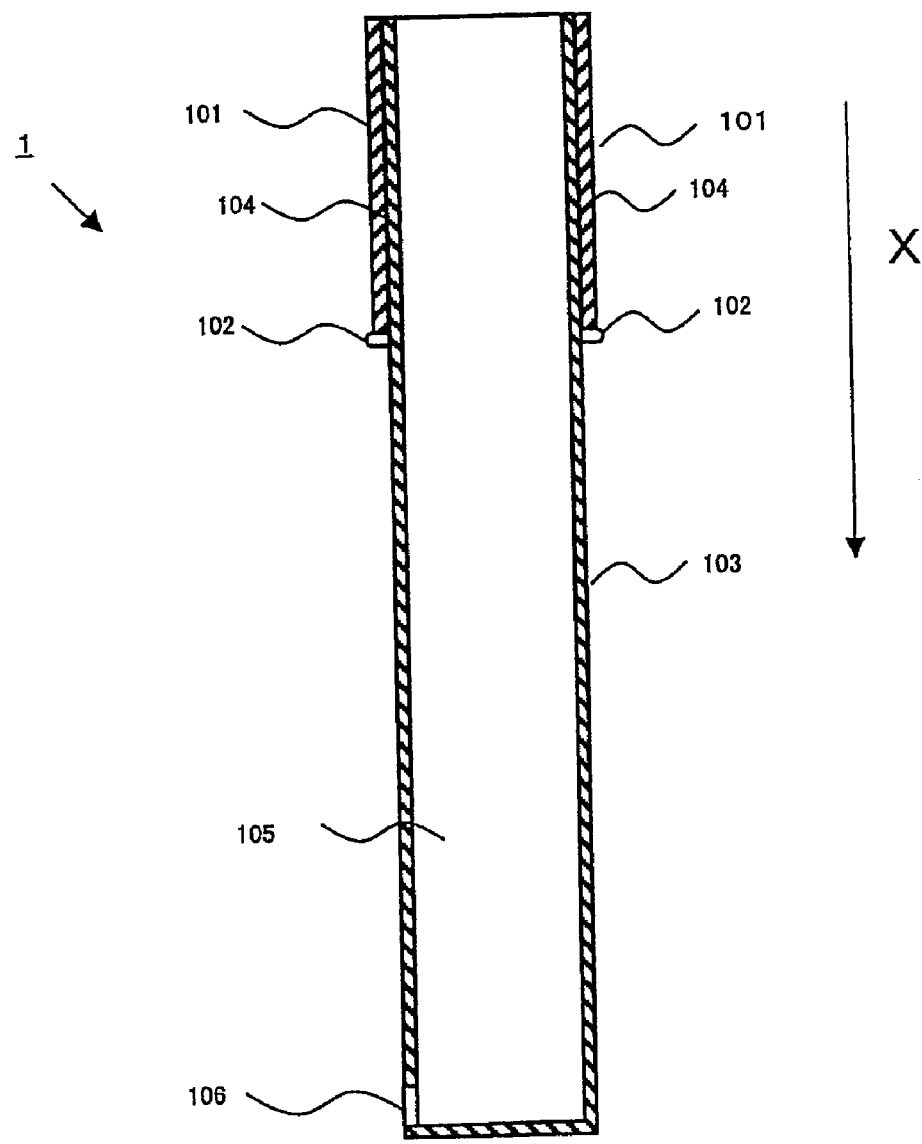
FIG. 2 A cross sectional view along the line A-A of the measurement cell 1 shown in FIG. 1.

One embodiment of the measurement cell in the present invention is described by using FIGS. 1 to 3. FIG. 1 is a perspective view illustrating a configuration of a measurement cell in Embodiment 1 of the present invention; FIG. 2 is a cross sectional view along the line A-A of the measurement cell 1 shown in FIG. 1; and FIG. 3 is a perspective view illustrating the measurement cell 1 shown in FIG. 1 with the protection cover 101 moved.

As shown in FIGS. 1 to 3, the measurement cell 1 in Embodiment 1 is configured with mainly two members, i.e., a main body 103 of a bottomed hollow quadrangular prism with an opening at the upper portion thereof, and a protection cover 101.

The main body 103 includes a sample holding part 105 for holding a sample, configured with the hollow portion inside the main body 103; an opening part 106 for supplying a sample to inside the sample holding part 105, communicating with the sample holding part 105; and an optical window portion 104 for allowing light to enter the sample holding part 105, and allowing light to exit the sample holding part 105.

The protection cover 101 is provided at the circumferential sides of the main body 103, to be movable along the circumference of the sample holding part 105 so as to cover and protect the optical window portion 104.

In the main body 103, a first protection-cover-holding part 102 for holding the protection cover 101 is provided at a position where the optical window portion 104 is covered. Before carrying out a measurement, the protection cover 101 is held by the first protection-cover-holding part 102 at the position where the optical window portion 104 of the main body 103 is covered. At this position, the protection cover 101 exposes the opening part 106.

To be more specific, the first protection-cover-holding part 102 is provided at the position where the optical window portion 104 is covered and the opening part 106 is exposed, and the protection cover 101 before carrying out a measurement is held by the first protection-cover-holding part 102 at the position where the optical window portion 104 of the main body 103 is covered and the opening part 106 is exposed.

The protection cover 101 can be moved along the circumferential sides of the main body 103 in the direction of arrow X. As shown in FIG. 3, when measuring, the measurement can be carried out with the optical window portion 104 exposed, by moving the protection cover 101 to pass over the first protection-cover-holding part 102. Therefore, measurement error based on the dirty and damaged optical window portion 104 can be prevented, since the optical window portion 104 is covered by the protection cover 101 without being exposed when not in measurement.

The optical window portion 104 in the measurement cell 1 is preferably formed by a material that is optically transparent or a material with substantially no absorption of visible light. For example, quartz, glass, polystyrene, and polymethyl methacrylate may be mentioned. In the case when the measurement cell 1 is to be made disposable, in view of costs, polystyrene is preferably used for the formation.

The first protection-cover-holding part 102 may be configured so that the protection cover 101 can be disposed at the position where the optical window portion 104 is covered before the measurement, and so that the protection cover 101 can expose the optical window portion 104 when in measurement. For example, the first protection-cover-holding part 102 can be configured by providing projections at a portion of the outer surface of the measurement cell. To be specific, for example, as shown in FIGS. 1 to 3, the first protection-cover-holding part 102 may be configured by providing projections (projection-like member) at the four corners connecting the side face and the side face of the hollow quadrangular prism of the main body 103.

The projections configuring the first protection-cover-holding part 102 is preferably formed by a material having elasticity, so as to allow the projections to deform to move the protection cover 101. For example, synthetic rubber such as natural rubber, isoprene rubber, and Teflon® rubber may be mentioned. By using any one of such materials, and by applying force to at least one of the protection cover 101 and the main body 103 for deforming the projections configuring the first protection-cover-holding part 102, the protection cover 101 and the main body 103 are allowed to slide from each other, so that the protection cover 101 can be moved in the direction of arrow X.

Also, in the present invention, the projections may be provided at a portion of the side face of the hollow quadrangular prism, i.e., the main body 103, to form the first protection-cover-holding part 102.

Further, between the protection cover 101 and the main body 103, a sheet or layer (sheet-like or layer-like member) may be inserted to form the first protection-cover-holding part. The sheet or layer may be formed, for example, by thinly applying and drying sticky resins such as hydrogenated petroleum resin, rosin ester, special rosin ester, alkylphenol resin, water-soluble polymer, and emulsion resin to the inner surface of the protection cover 101 or the outer surface of the main body 103.

By using the first protection-cover-holding part configured with such a sheet or layer, the first protection-cover-holding part can hold the protection cover 101 based on the stickiness of the sticky resin. In this case, by sliding the protection cover 101 and the main body 103 from each other with the application of force exceeding the stickiness of the sticky resin to at least one of the protection cover 101 and the main body 103, the protection cover 101 can be moved in the direction of arrow X.

As still another embodiment, an elastic part configured with the material having elasticity may be formed at least a portion of the main body 103 contacting the protection cover 101, to form the first protection-cover-holding part. By forming such an elasticity part, by sliding the protection cover 101 and the main body 103 from each other with application of force that is enough to deform the elasticity part to at least one of the protection cover 101 and the main body 103, the protection cover 101 can be moved to the direction of arrow X.

The first protection-cover-holding part may also be configured with the member having a form of check valve or leaf spring, and may also be configured with a material other than the material mentioned above. With such an arrangement, the configuration that disables the protection cover 101 to move in the direction opposite to the direction of arrow X shown in FIGS. 1 to 3 can be provided. That is, the configuration can be made so that the protection cover 101 is unable to move from the part of the main body 103 lower than the first protection-cover-holding part 102 and not including the optical window portion 104, to the part of the main body 103 upper than the first protection-cover-holding part 102 and including the optical window portion 104. With such an arrangement, when the optical window portion is mistakenly exposed before use, it can be easily known that the measurement cell is unusable.

The first protection-cover-holding part can be configured by forming the main body 103 and the projections integrally. In this case, the main body 103 and the first protection-cover-holding part are made with the same material, and the projections are made with the material having no elasticity and stickiness. However, the projections can be broken to move the protection cover 101 in the direction of arrow X.

Embodiment 2

Figure 4:
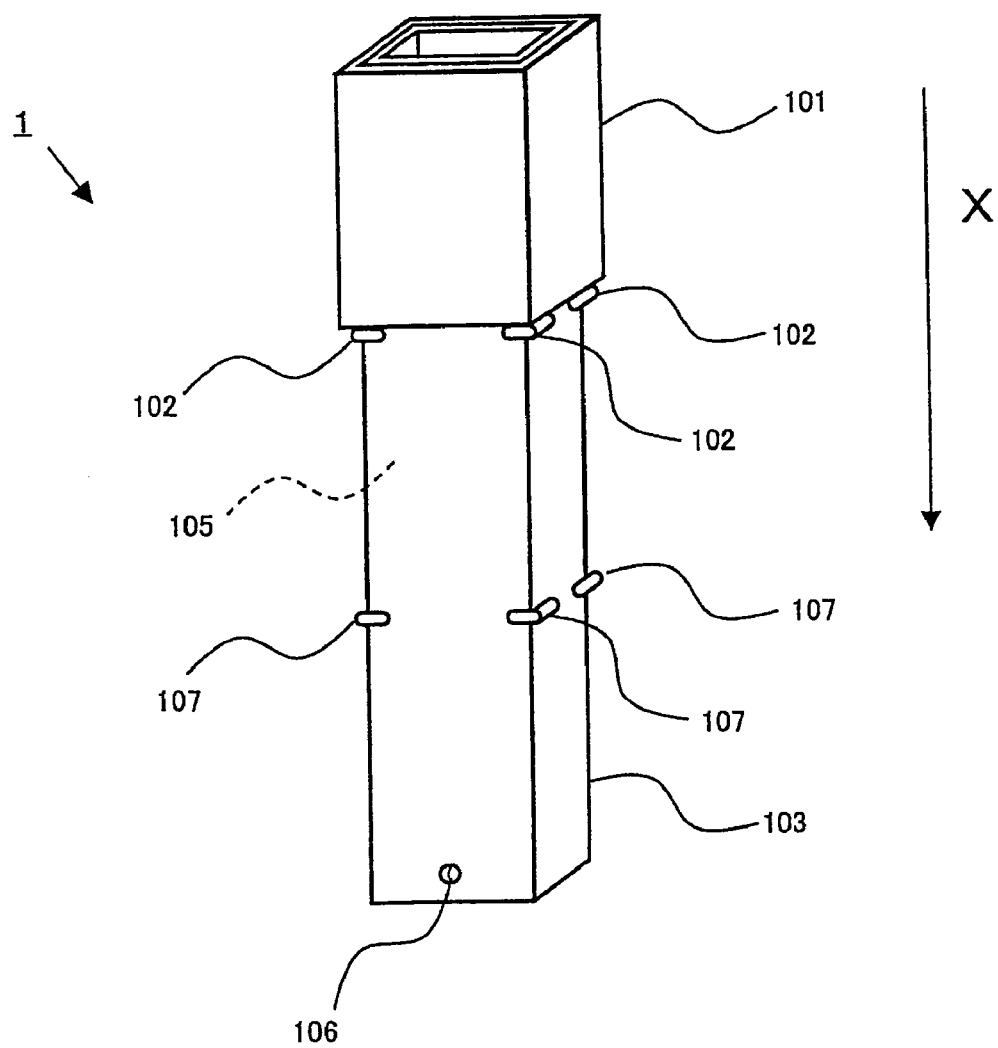
FIG. 4 A perspective view illustrating a measurement cell 1 in Embodiment 2 of the present invention.

The configuration of a measurement cell in another embodiment of present invention is described by using FIGS. 4 and 5. FIG. 4 is a perspective view illustrating a configuration of a measurement cell 1 in Embodiment 2 of the present invention, and FIG. 5 is a perspective view illustrating the measurement cell 1 shown in FIG. 4 with the protection cover 101 moved.

As shown in FIGS. 4 and 5, other than further providing a second protection-cover-holding part 107 for holding the protection cover 101 at the position where the optical window portion 104 and the opening part 106 are exposed, the configuration of the measurement cell 1 in Embodiment 2 is the same as that of the measurement cell 1 in Embodiment 1.

As shown in FIG. 4, before carrying out measurement, the protection cover 101 is held by the first protection-cover-holding part 102 at the position where the optical window portion 104 of the main body 103 is covered. At this position, the protection cover 101 exposes the opening part 106. The protection cover 101 can be moved in the direction of arrow X, along the circumferential sides of the main body 103. As shown in FIG. 5, when measuring, the protection cover 101 can be moved to pass over the first protection-cover-holding part 102, so that measurement can be carried out with the optical window portion 104 exposed. With such an arrangement, since the optical window portion 104 is protected by the protection cover 101 when not in measurement, measurement error due to dirt and damage on the optical window portion 104 can be prevented.

In Embodiment 2, as shown in FIG. 5, the protection cover 101 is held by the second protection-cover-holding part 107 at the position shown in FIG. 5 (that is, a position where the optical window portion 104 and the opening part 106 are exposed). With such an arrangement, the opening part 106 can be reliably exposed without allowing the protection cover 101 to move to the position where the opening part 106 is covered. Therefore, a sample can be supplied easily from the opening part 106 to inside the sample holding part 105 while the optical window portion 104 is exposed, and measurement can be carried out at the optical window portion 104.

Figure 6:
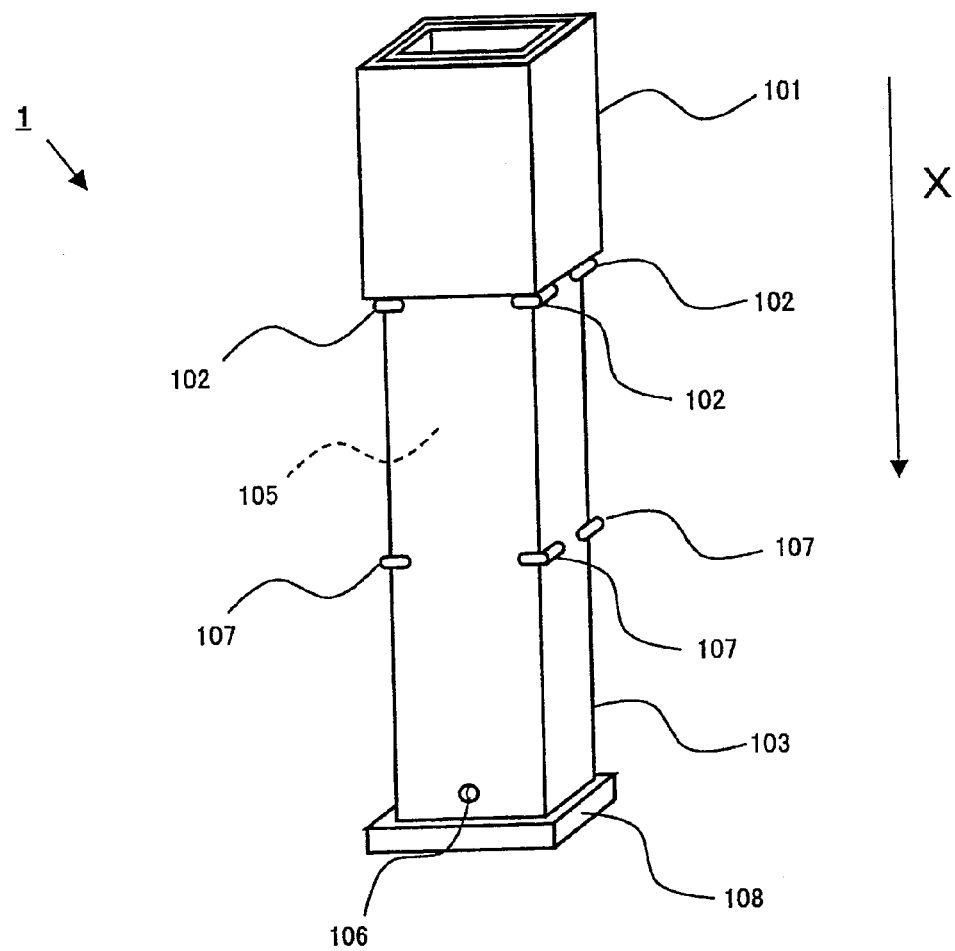
FIG. 6 A perspective view illustrating a configuration of a measurement cell 1 in Embodiment 3 of the present invention.

The second protection-cover-holding part 107 may have the same configuration as that of the first protection-cover-holding part 102, or may have different configuration. However, as shown in FIGS. 5 and 6, the second protection-cover-holding part 107 is preferably configured with a projection-formed member, as in the case of the first protection-cover-holding part 104 in Embodiment 1. With such an arrangement, by applying force to at least one of the protection cover 101 and the main body 103 with the force enough to deform the projections configuring the second protection-cover-holding part 107 to slide the protection cover 101 and the main body 103 from each other, the protection cover 101 can be moved further to the direction of arrow X.

As necessary, when the protection cover 101 is at the position shown in FIG. 5, the protection cover 101 can be further moved back to the position shown in FIG. 4 by moving the protection cover 101 to the direction opposite to the direction of arrow X, by applying force that is enough to deform the projection configuring the first protection-cover-holding part 102 to at least one of the protection cover 101 and the main body 103, to slide the protection cover 101 and the main body 103 from each other.

Embodiment 3

Figure 7:
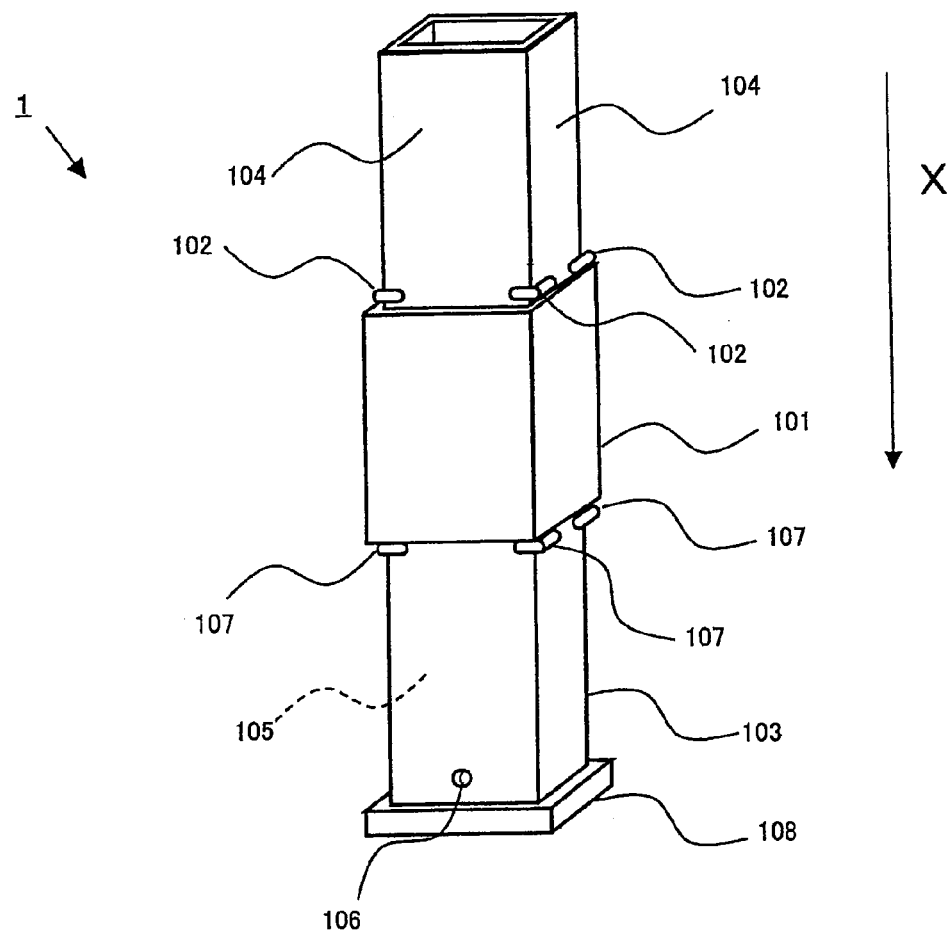
FIG. 7 A perspective view illustrating the measurement cell 1 shown in FIG. 6 with the protection cover 101 moved.

A configuration of a measurement cell in still another embodiment of the present invention is described next by using FIGS. 6 to 8. FIG. 6 is a perspective view illustrating a configuration of a measurement cell 1 in Embodiment 3 of the present invention; FIG. 7 is a perspective view illustrating the measurement cell 1 shown in FIG. 6 with the protection cover 101 moved; and FIG. 8 is a perspective view illustrating the measurement cell 1 shown in FIG. 7 with the protection cover 101 further moved.

Figure 8:
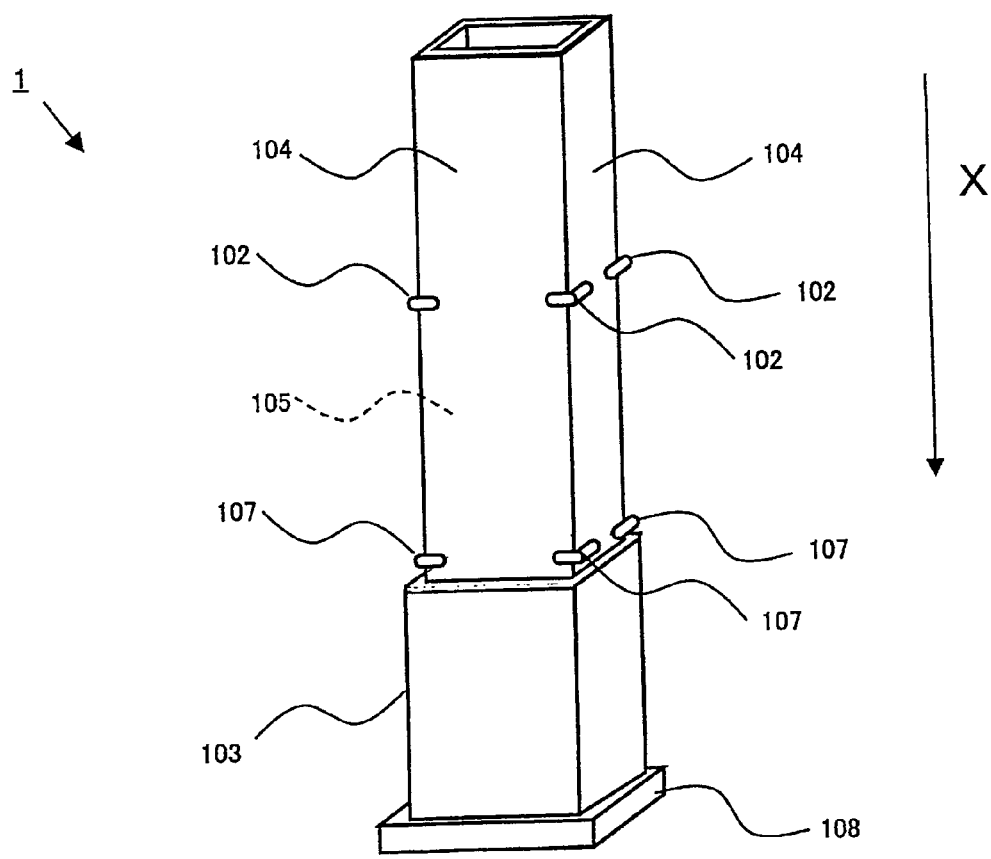
FIG. 8 A perspective view illustrating the measurement cell 1 shown in FIG. 7 with the protection cover 101 further moved.

As shown in FIGS. 6 to 8, the measurement cell 1 in Embodiment 3 has the same configuration with the measurement cell 1 in Embodiment 2 above, except that a third protection-cover-holding part 108 for holding the protection cover 101 at the position where the opening part 106 is covered is further provided.

As shown in FIG. 6, before measurement, the protection cover 101 is held at the position where the optical window portion 104 of the main body 103 is covered by the first protection-cover-holding part 102. At this position, the protection cover 101 exposes the opening part 106. The protection cover 101 can be moved in the direction of arrow X along the circumferential sides of the main body 103. As shown in FIG. 7, when measuring, the measurement can be conducted by moving the protection cover 101 to pass over the first protection-cover-holding part 102 to expose the optical window portion 104. With such an arrangement, the optical window portion 104 is covered by the protection cover 101 without being exposed when not in measurement, and therefore measurement error due to dirt and damage on the optical window portion 104 can be prevented.

As shown in FIG. 7, the protection cover 101 is also held at the position shown in FIG. 7 by the second protection-cover-holding part 107 (that is, a position where the optical window portion 104 and the opening part 106 are exposed). With such an arrangement, the opening part 106 can be exposed reliably without allowing the protection cover 101 to move to the position where the opening part 106 is covered, and therefore a sample can be easily supplied into the sample holding part 105 from the opening part 106 while the optical window portion 104 is exposed to conduct measurement at the optical window portion 104.

Further, in Embodiment 3, as shown in FIG. 8, the protection cover 101 can be further moved in the direction of arrow X after the measurement, to hold the protection cover 101 at the position where the opening part 106 is covered by the third protection-cover-holding part 108. With such an arrangement, the sample attached near the opening part 106 when the sample is supplied into the sample holding part 105 from the opening part 106 can be covered by the third protection-cover-holding part 108, and therefore a user can be prevented from mistakenly touching the sample.

Although the third protection-cover-holding part 108 may have the same configuration with the first protection-cover-holding part 104 and the second protection-cover-holding part 107, in the measurement cell 1 in Embodiment 3 as shown in FIGS. 6 to 8, the third protection-cover-holding part 108 is configured with a plate-like member provided at the lower end of the main body 103. Upon providing the plate-like member, a plate-like member having an area larger than the cross sectional area of the hollow cylindrical member of the main body 103 is provided to hold the protection cover 101 slided. Since the protection cover 101 does not have to be further moved in direction of arrow X to pass over the third protection-cover-holding part 108, for the material for configuring the plate-like member, the material having elasticity or stickiness does not have to be used.

The interval between the first protection-cover-holding part 102 and the second protection-cover-holding part 107, and the interval between the second protection-cover-holding part 107 and the third protection-cover-holding part 108 may be appropriately adjusted depending on the size of the main body 103 and the protection cover 101. However, as is mentioned later, such an interval is preferably set so that when the measurement cell 1 is immersed in a sample such as urine and when the sample is supplied to inside the measurement cell 1, the protection cover 101 as well is not immersed in the sample.

In the measurement cell 1 of the present invention as shown in Embodiments 1 to 3, an absorbent is preferably disposed at the inner side of the protection cover 101. With such an arrangement, when the protection cover 101 is moved along the circumferential sides of the main body 103, the absorbent disposed at the inside the protection cover 101 can wipe off the sample attached to the side face of the main body 103. Particularly, after measurement, as shown in FIG. 8, upon moving the protection cover 101 to the position where the opening part 106 is covered, the sample attached near the opening part 106 can be wiped off.

The form and area of the absorbent may be adjusted appropriately so that the absorbent is positioned at least the portion near the opening part 106 (that is, the portion corresponding to the opening part 106 and its vicinity) when the protection cover 101 is moved to the position where the opening part 106 is covered. This is because when the absorbent is configured with such conditions, the sample attached near the opening part 106 can be wiped off further reliably.

Therefore, the form of the absorbent is not particularly limited and the absorbent may be for example strip (band) or sheet. The absorbent may be provided, at least the opening part 106 side in the inner surfaces of the protection cover 101. The absorbent may also be provided at other inner surfaces, or at all the inner surfaces.

For the material for configuring the absorbent, for example, a polymer absorbent sheet using absorbing resin such as cross-linked polyacrylate made of acrylic acid may be mentioned.

The measurement cell of the present invention may further include a suction opening for sucking a sample into the sample holding part. In Embodiments 1 to 3 above, the opening at the upper end of the hollow cylindrical member of the measurement cell 1 as shown in FIGS. 1 to 8 may be used as the suction opening.

The measurement cell of the present invention may be further provided with a reagent that reacts specifically with the analyte in the sample, in the sample holding part. The reagent is preferably provided in the sample holding part in dried condition, to be dissolved in the sample when the sample is supplied into the sample holding part. For example, the reagent may be carried by impregnating a porous carrier made of glass fiber or filter paper with a reagent solution, drying the reagent solution, and providing the porous carrier in the sample holding part. The reagent may be disposed by applying the reagent solution directly to the sidewall face configuring the sample holding part, and then drying.

For the reagent, for example, enzyme, antibody, hormone receptor, chemiluminescence reagent, and DNA may be mentioned. Especially, antibodies are advantageous in that reagents are easily made, since antibodies can be produced with known methods. For example, by immunizing mice or rabbits using proteins such as albumin, and hormones such as hCG and LH as antigen, antibodies to these antigens can be obtained. For the antibody, an antibody to a protein included in urine such as albumin, and an antibody to a hormone included in urine such as hCG and LH may be mentioned.

For the sample in the present invention, may be mentioned are body fluids such as urine, serum, plasma, and blood; and liquids such as a culture supernatant fluid. Among these, urine is preferable as a sample. When the sample is urine, daily health management can be done at home noninvasively.

For the analyte, albumin, hCG, LH, CRP, and IgG may be mentioned.

In qualititative analysis on urine conducted at an earlier stage of health management, the following twelve items are examined: pH, specific gravity, protein, sugar, occult blood, ketones, bilirubin, urobilinogen, nitrite, leukocyte, ascorbic acid, amylase, and sodium chloride. On analyzing kidney function, microalbumin can be mentioned, and for a pregnancy test marker, hormones such as hCG and LH can be mentioned. For proteins, microalbumin, and hormones such as hCG and LH, optical measurement based on antigen-antibody reaction is suitable. For the optical measurement based on antigen-antibody reaction, nephelometric immunoassay, turbidimetric immunoassay, and latex agglutination may be mentioned.

Embodiment 4

2. Method for Using Measurement Cell

Figure 9:
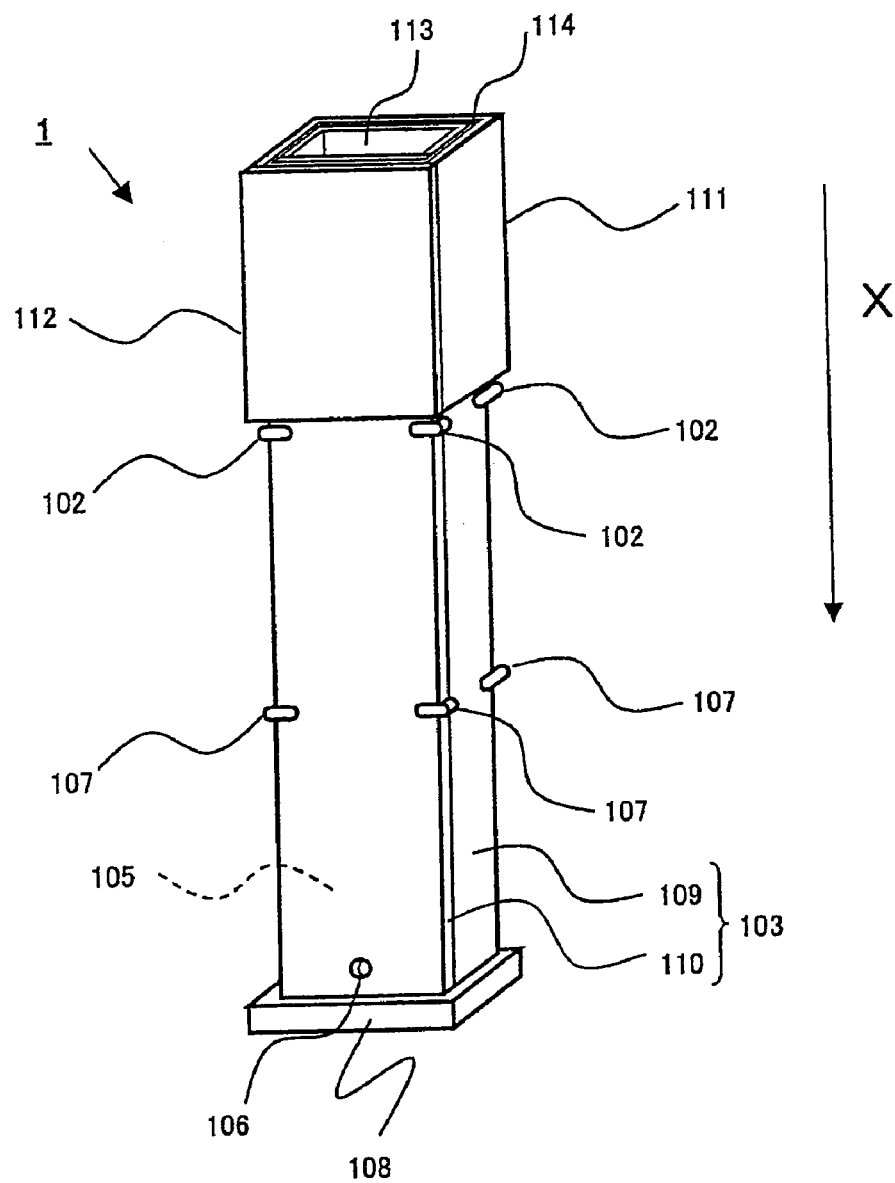
FIG. 9 A perspective view illustrating a configuration of a measurement cell in Embodiment 4 of the present invention.
Figure 10:
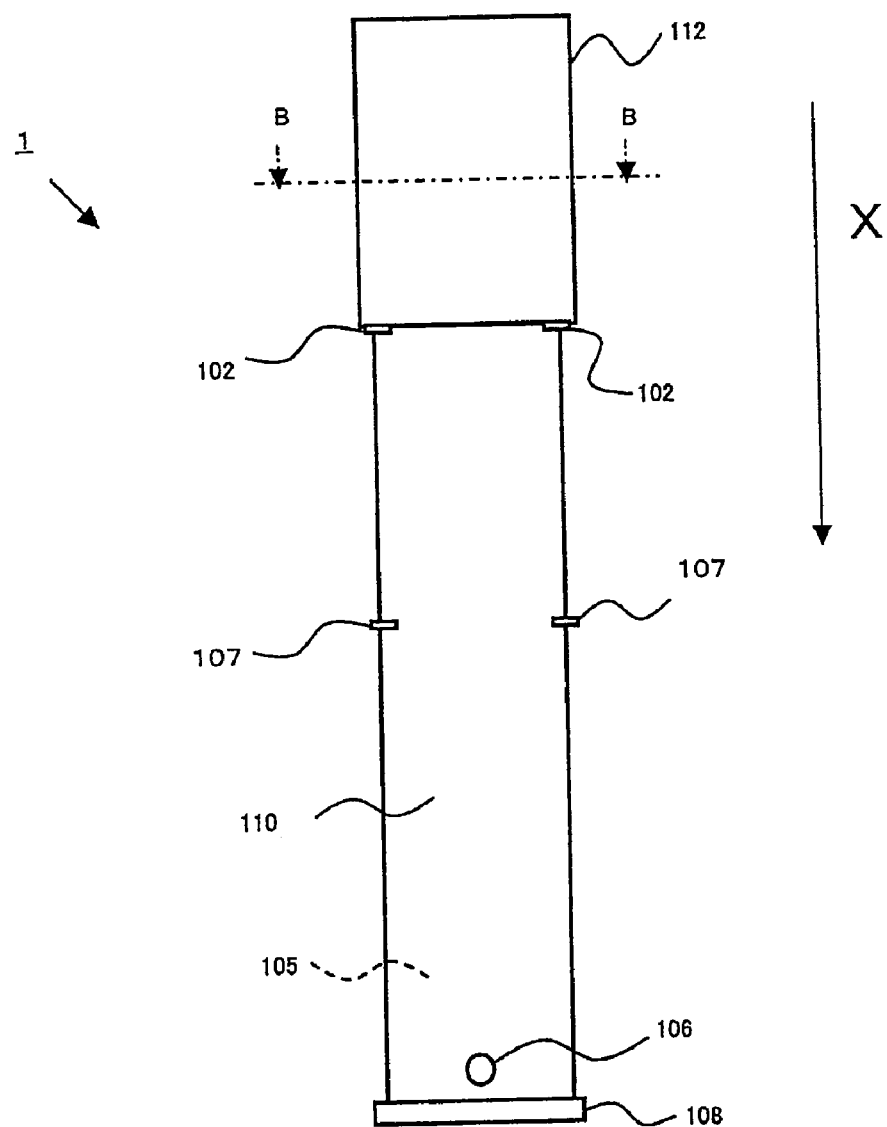
FIG. 10 A front view of the measurement cell 1 shown in FIG. 9.
Figure 11:
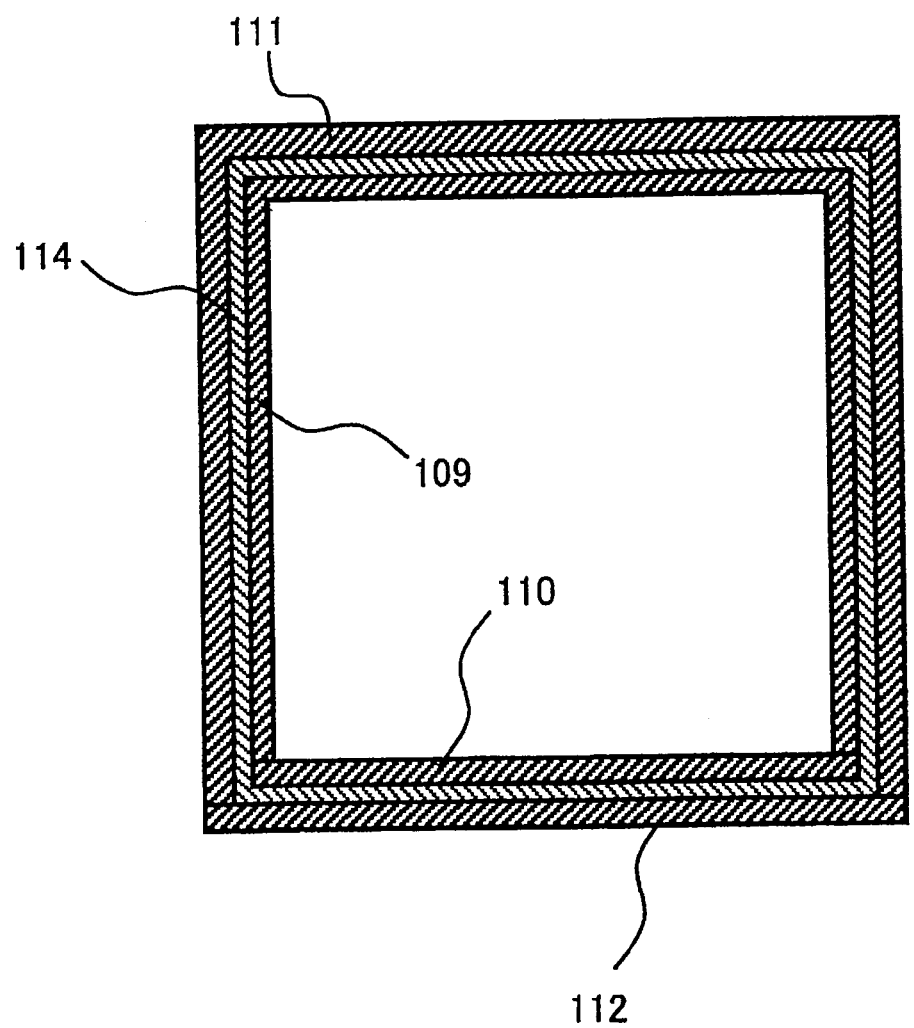
FIG. 11 A cross section along the line B-B of the measurement cell 1 shown in FIG. 10.

In the following, a method for using a measurement cell of the present invention (that is, a measurement method using a measurement cell) is described by referring to the figures. Described in this section is the case when a measurement cell (Embodiment 4), which is a modified embodiment of the measurement cell in Embodiment 3 above, is used, and the sample is urine, and analyte is human albumin. FIG. 9 is a perspective view illustrating a measurement cell in Embodiment 4 of the present invention; FIG. 10 is a front view of the measurement cell 1 shown in FIG. 9; and FIG. 11 is a cross sectional view along the line B-B of the measurement cell 1 shown in FIG. 10.

In a measurement cell 1 of Embodiment 4, the main body 103 is configured to include a first measurement cell member 109 and a second measurement cell member 110. The measurement cell 1 in this Embodiment is almost the same as that of the Embodiment 3, except that the main body 103 of hollow quadrangular prism, in which a hollow portion functioning as the sample holding part 105 is formed, by combining the first measurement cell member 109 and the second measurement cell member 110, and that an absorbent 114 is provided at the inner surface of the protection cover 101.

The sample holding part 105 is a hollow portion of quadrangular prism with a base of about 5 to 12 mm per side, and a height of about 50 to 100 mm. The measurement cell 1 is provided with an opening part 106 for supplying a sample into the sample holding part 105 and a suction opening 113 for sucking a sample into the sample holding part 105. Each of the opening part 106 and the suction opening 113 is communicating with the sample holding part 105.

The main body 103 includes a first protection-cover-holding part 102 for holding the protection cover at the position where the optical window portion 104 is covered; and a second protection-cover-holding part 107 for holding the protection cover at the position where the optical window portion 104 and the opening part 106 are exposed. Further, a third protection-cover-holding part 108 for holding the protection cover 101 at the position where the opening part is covered is combined with the main body 103, covering the opening facing the suction opening 113 of the main body 103.

The protection cover 101 is configured by assembling the first protection cover member 111 and the second protection cover member 112, and as shown in FIG. 11, at the inner surface of the protection cover 101, an absorbent 114 is disposed.

The first measurement cell member 109, the second measurement cell member 110, the first protection cover member 111, the second protection cover member 112, and the third protection-cover-holding part 108 are made of transparent polystyrene. For the absorbent 114, a polymer absorbent sheet made of polyethylene oxide is used.

As shown in FIG. 9, before conducting measurement, the protection cover 101 is held by the first protection-cover-holding part 102 at the position where the optical window portion 104 of the main body 103 is covered. The protection cover 101 can also be moved in the direction of arrow X, along the circumferential sides of the main body 103. In the measurement cell 1 in this Embodiment, since the optical window portion 104 is protected by the protection cover 101 without being exposed when not measuring, measurement error based on dirt and damage on the optical window portion 104 can be prevented.

A method for manufacturing the measurement cell 1 in Embodiment 4 is described next by referring to FIG. 12. FIG. 12 is an exploded perspective view of the measurement cell 1 in Embodiment 4.

The first measurement cell member 109, the second measurement cell member 110, and the first protection cover member 111 are made of transparent polystyrene, and can be made by molding with a metal mold. For the molding, known resin molding technique may be used. The upper side and the ends of the first measurement cell member 109 and the first protection cover member 111 are opened, as shown in FIG. 12, thereby forming a depressed portion.

The first measurement cell member 109 is provided with two projections functioning as the first protection-cover-holding part 102, and two projections functioning as the second protection-cover-holding part 107. The second measurement cell member 110 is provided with an opening part 106, two projections functioning as the first protection-cover-holding part 102, and two projections functioning as the second protection-cover-holding part 107.

In the two walls facing each other in the first measurement cell member 109, the area between an opening near the first protection-cover-holding part 102 and the first protection-cover-holding part 102 functions as the optical window portion 104.

Then, the reagent-holding part 115 is formed at the bottom face of the depressed portion of the first measurement cell member 109. For example, by dropping a predetermined amount of an aqueous solution of an antibody against human albumin, i.e., a reagent for optical measurement, to the bottom portion of the depressed portion of the first measurement cell member 109 to apply the reagent, by using for example a microsyringe, and allowing to stand in an environment with temperature of ambient temperature to 30° C. to evaporate moisture, the reagent can be carried in dry condition. The concentration of the aqueous solution of antibody, the amount to be dropped, and the area to be dropped are, for example, a concentration of 11 µg/mL, an amount of 0.1 mL, and an area of 1.5 cm$^2$, respectively.

The concentration and the amount of the aqueous solution including the reagent to be applied may be adjusted appropriately depending on the required characteristics of the measurement cell and space limitations from the position in the first measurement cell member 109. The position and the area of the reagent-holding part 115 in the first measurement cell member 109 may be adjusted appropriately in view of the solubility of reagent in the sample and the position of the optical window portion 104.

The antibody against human albumin can be obtained by conventionally known methods. For example, by refining rabbit antiserum immunized with human albumin with a protein A column chromatography, and dialyzing with a dialysis tube, the anti-human albumin antibody can be obtained.

The second protection cover member 112 and the third protection-cover-holding part 108 are transparent polystyrene-made plate members, and as the first measurement cell member 109, the second measurement cell member 110, and the first protection cover member 111, can be made by molding with a metal mold. Instead, these may also be formed by cutting a resin-made plate into a desired form.

The first measurement cell member 109, the second measurement cell member 110, and the third protection-cover-holding part 108 that can be obtained as described above are bonded with the positional relation shown by the broken lines shown in FIG. 12, to assemble the main body. That is, after applying an adhesive such as an epoxy resin at the joint portion of each member, each member is put together and allowed to stand to be dried. Instead, the joint portions may be also welded, for example, by heat or ultrasonic waves by using a commercially available welding device after each member was put.

Then, the absorbent 114, which is made of a water-absorbing polymer resin sheet, is wrapped around on the left end side of the assembled main body as shown in FIG. 12. The first protection cover member 111 and the second protection cover member 112 are bonded with the positional relation shown with the broken lines in FIG. 12, so as to cover the sheet wrapped around, thereby assembling the protection cover around the main body. In this case as well, at the joint portion of each member, an adhesive such as an epoxy resin is applied, and then each member is allowed to stand to dry the joint portion for assembly. The first protection cover member 111 and the second protection cover member 112 may also be welded by heat or ultrasonic waves at the joint portion, by using for example commercially available welding devices. The measurement cell 1 in Embodiment 4 with the configuration as shown in FIG. 9 can be obtained.

The size of the measurement cell 1, and the length and space between each members may be adjusted appropriately, as long as the effects of the invention are not damaged. For example, the size may be the following.

First measurement cell member 109
  Thickness of 1 mm
  Size of the depressed portion
  Width of 8 mm, Depth of 8 mm, Length of 96 mm Second measurement cell member 110
  Thickness of 1 mm, Width of 10 mm, Length of 96 mm
  Third protection-cover-holding part 108
  Thickness of 1 mm, Length and Width of 14 mm First protection cover member 111
  Thickness of 1 mm
  Size of the depressed portion
  Width of 12 mm, Depth of 12 mm, Length of 14 mm Second protection cover member 112
  Thickness of 1 mm, Length and Width of 14 mm

3. Measurement Device

Figure 13:
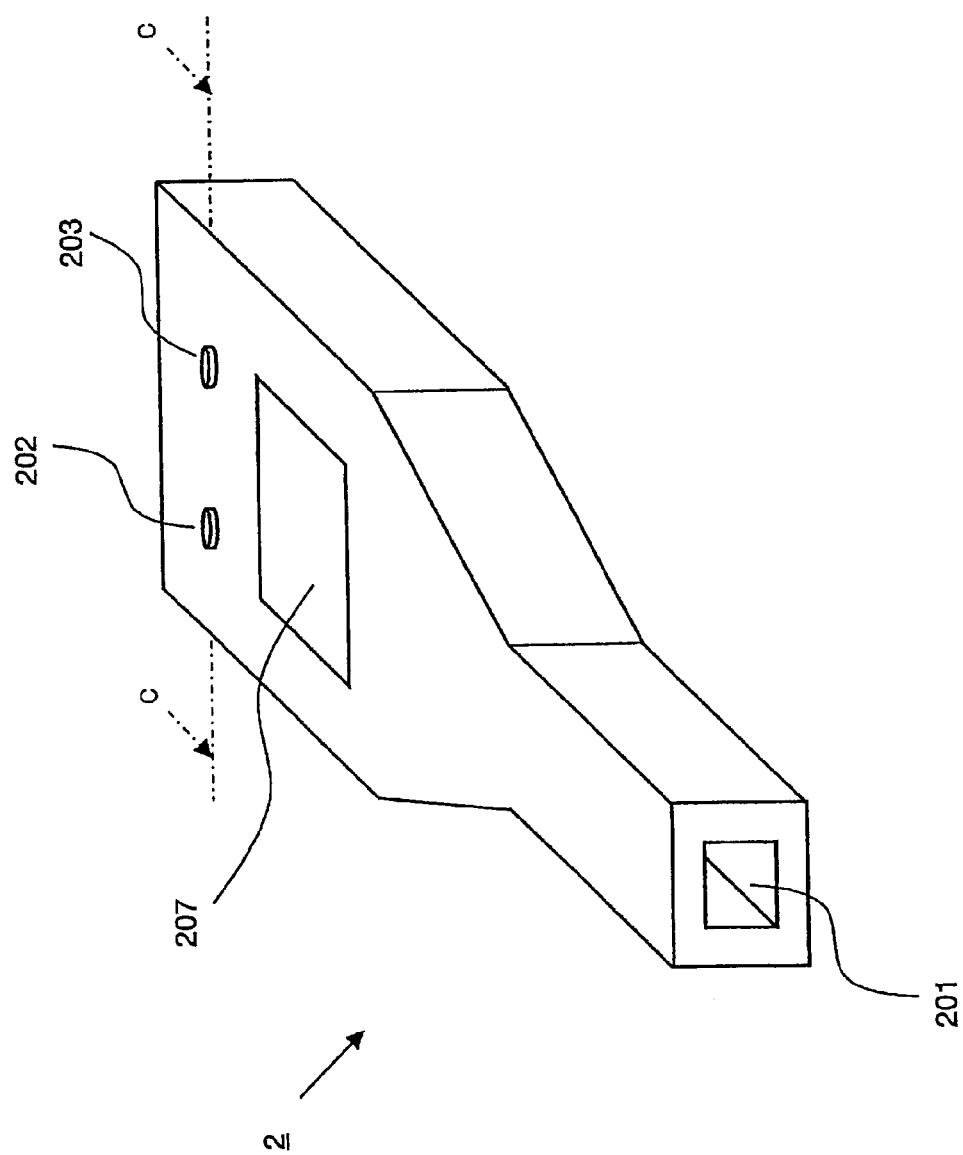
FIG. 13 A perspective view illustrating a measurement device 2 using the measurement cell 1 of Embodiment 4.
Figure 14:
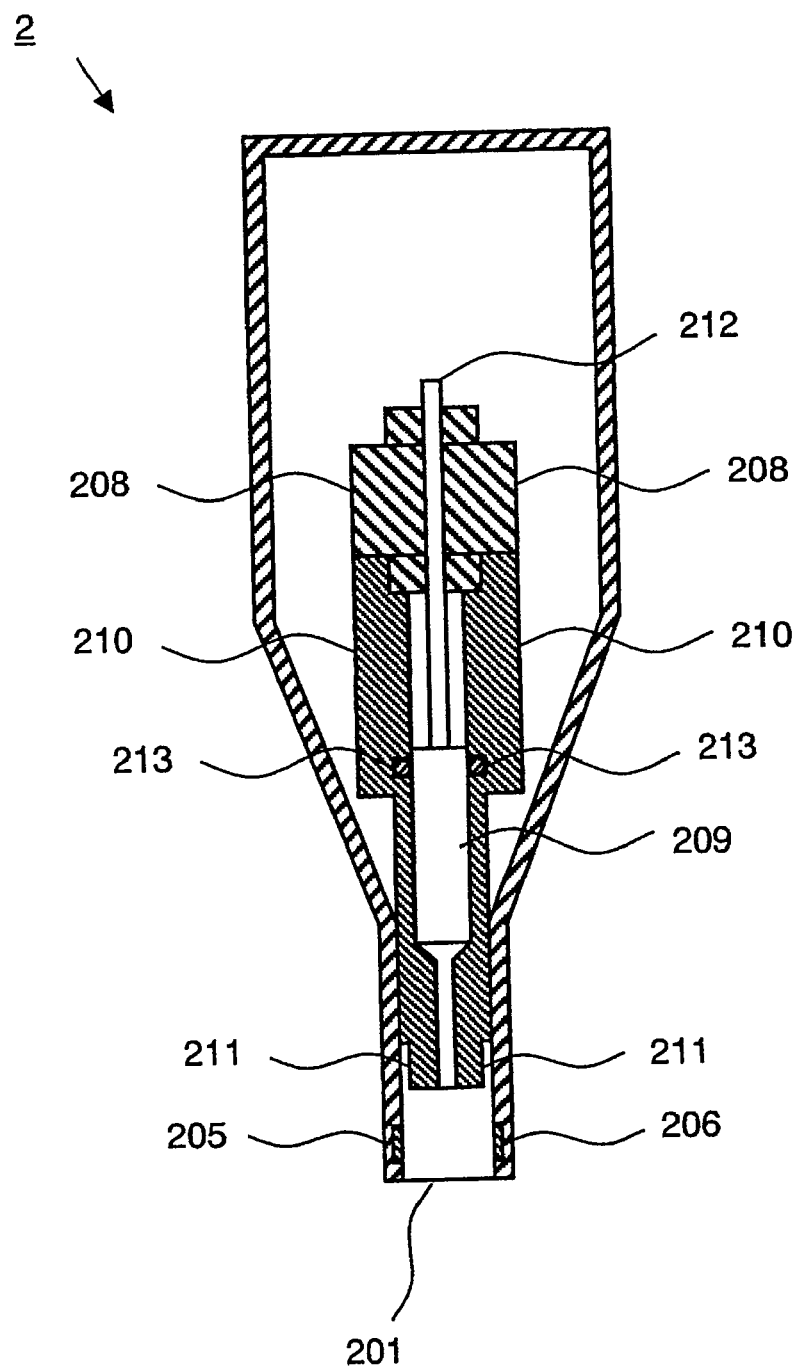
FIG. 14 A cross sectional view illustrating the measurement device 2 shown in FIG. 13.
Figure 15:
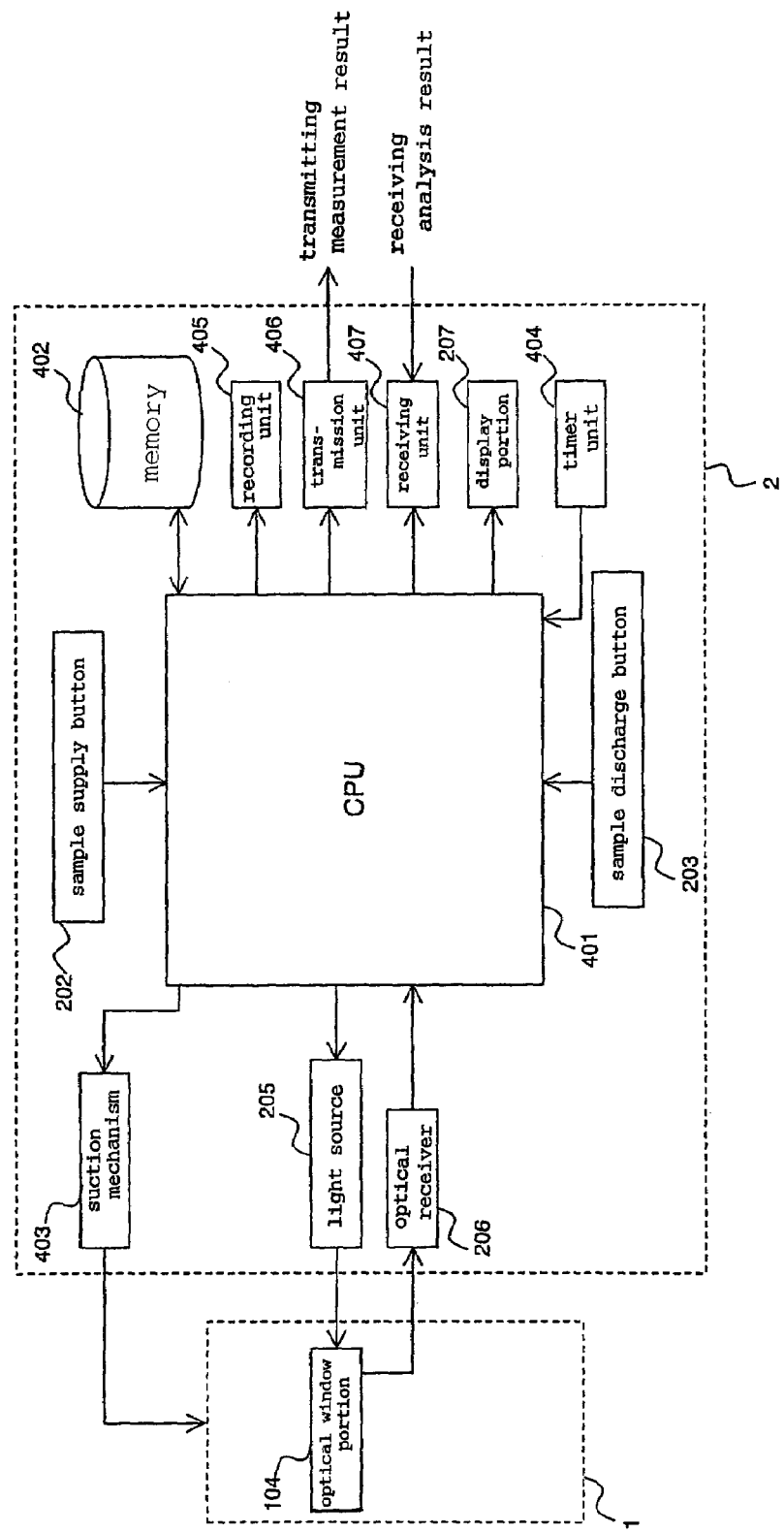
FIG. 15 A block diagram illustrating a configuration of the measurement device 2 shown in FIGS. 13 and 14.

A measurement device using the measurement cell of the present invention is described next with reference to FIGS. 13 to 15, by referring to a measurement device using the measurement cell in Embodiment 4 described above as a typical example. FIG. 13 is a perspective view illustrating a measurement device 2 using the measurement cell 1 in Embodiment 4; FIG. 14 is a cross sectional view illustrating the measurement device 2 shown in FIG. 13; and FIG. 15 is a block diagram illustrating a configuration of the measurement device 2 shown in FIGS. 13 and 14.

As shown in FIG. 13, the measurement device 2 in this Embodiment includes: a measurement cell attaching portion 201 for removably attaching the measurement cell 1; a sample supply button 202 for supplying a sample to the measurement cell 1; a sample discharge button 203 for discharging the sample in the measurement cell 1 to for example a paper cup after the measurement; and a display portion 207, i.e., a liquid crystal display, for showing the measurement result. The opening part of the measurement cell attaching portion 201 is given a size so as to allow the insertion of the main body of the measurement cell but disallow the insertion of the protection cover 101. For example, when the measurement cell 1 in Embodiment 4 is used, the size of the opening part may be 10.5 mm in length and width.

As shown in FIG. 14, a measurement cell attach-detach portion 211 is provided at the inner side of the measurement cell attaching portion 201, and the measurement cell attach-detach portion 211 is inserted into the suction opening 113 of the measurement cell 1 when attaching the measurement cell 1. For preventing air leakage at the joint portion when attaching the measurement cell 1, a seal ring made of elastic resin such as Teflon® and isoprene rubber is preferably provided around the measurement cell attach-detach portion 211 to improve the adhesion between the measurement cell attach-detach portion 211 and the suction opening 113.

As shown in FIG. 14, the measurement device 2 further includes: a motor 208 for moving a plunger 209 disposed inside the cylinder 210 through a plunger joint 212; a light source 205 for allowing incident light entered the optical window portion 104 of the measurement cell 1 to exit; and an optical receiver 206 for receiving the exit light from the optical window portion 104 of the measurement cell 1. The motor 208, the plunger 209, and the cylinder 210 correspond to the suction mechanism 403 for sucking the sample into the sample holding part 105 of the measurement cell 1. In the cylinder 210, an O-ring 213 is provided to keep the hermeticity between the cylinder 210 and the plunger 209.

As shown in FIG. 15, in the measurement device 2, a CPU 401, i.e., a computing unit for detecting or determining the quantity of the analyte included in the sample based on the exit light received by the optical receiver 206; and a memory 402, i.e., a memory unit which stores a calibration curve showing relations between the concentration of the analyte, i.e., human albumin, and the exit light intensity received by the optical receiver 206 are provided.

For the light source 205 in the measurement device 2, a semiconductor laser which outputs light with a wavelength of 650 nm may be used. A light emitting diode (LED) may also be used instead. Although measurement based on turbidimetric immunoassay is used and a wavelength of 650 nm for light application and light reception is selected in this Embodiment, such a wavelength and a measurement method may be appropriately selected according to measurement subject.

For the optical receiver 206 in this Embodiment, photodiode is used. For the optical receiver 206, a charge coupled device (CCD) and a photo multimeter may also be used instead.

The suction mechanism 403 in the measurement device 2 is configured so that the plunger 209 in the cylinder 210 is operated by the motor 208, which is a linear-type step motor.

The step motor is a motor which rotates in a particular rotation angle per one pulse signal inputted, and therefore the rotation angle can be determined by the pulse count and an encoder for positioning is unnecessary. That is, the operating distance of the plunger (piston) can be controlled based on the pulse count entered. The rotation of the motor is converted to linear motion by using a gear mechanism and a linear mechanism in which a male screw and a female screw are combined to operate the plunger. In linear-type step motors, a linear mechanism in which a male screw and a female screw are combined in a motor is incorporated, and the configuration is made so that the plunger joint, which is a rod-like movable part, generates linear motion based on the pulse count entered. Thus, the plunger may be directly connected to the plunger joint, for simple configuration.

4. Method of Using Measurement Device

With reference to a method of using a measurement device in which a measurement cell of the present invention is used, steps for measuring an analyte in a sample by using the measurement cell 1 in Embodiment 4 and the measurement device 2 in the above are described by referring to FIGS. 16 to 22. FIGS. 16 to 22 are diagrams for describing steps for measuring the analyte in a sample by using the measurement cell 1 and the measurement device 2 of the present invention. In the following, an example using urine as a sample is described. In FIGS. 16 to 22, for clear view of the structure inside the measurement cell, the size of the measurement cell relative to the measurement device is drawn larger than the actual size.

Figure 16:
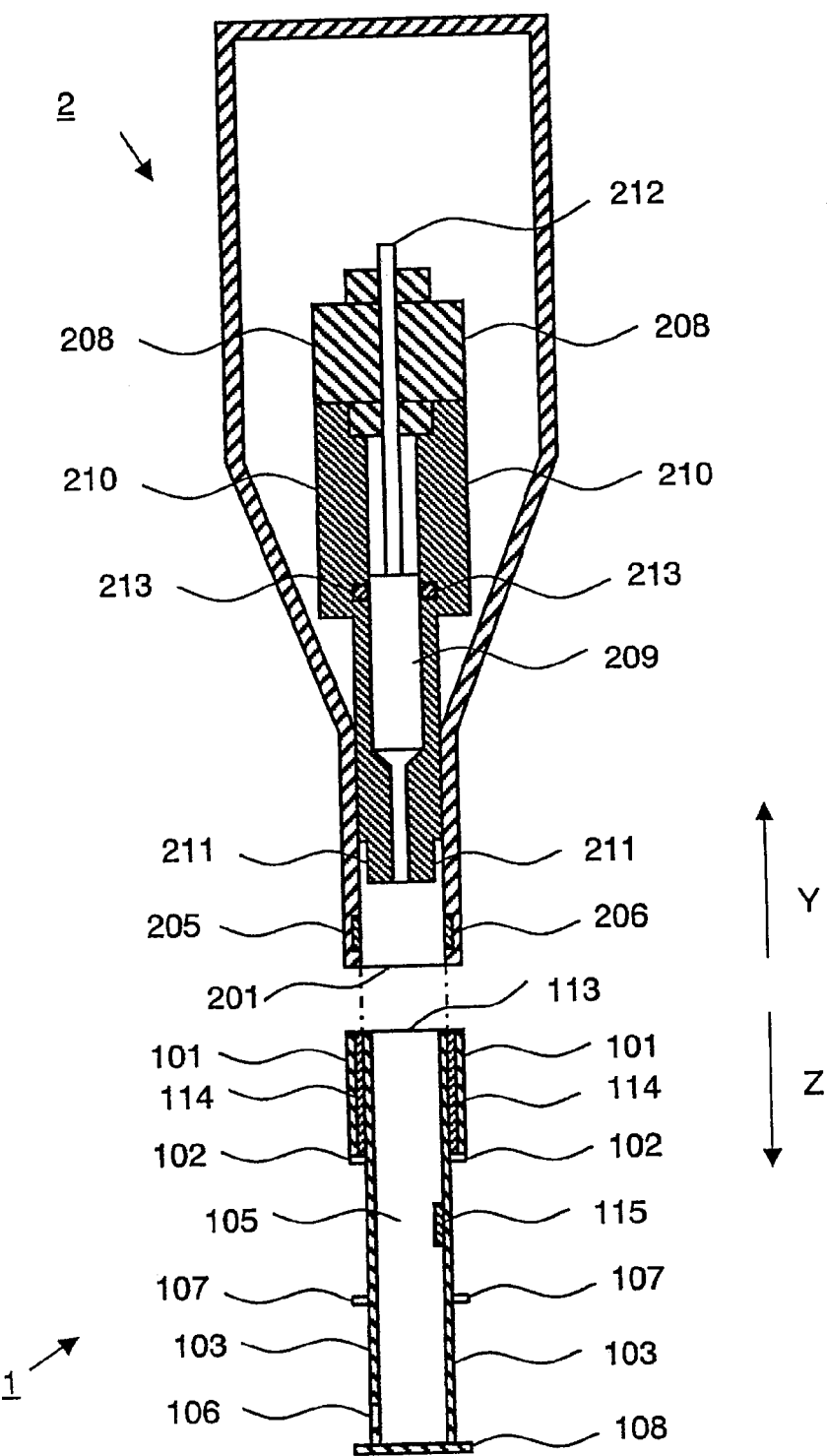
FIG. 16 A diagram for describing a step in the steps for measuring an analyte in a sample by using a measurement cell 1 and a measurement device 2 of the present invention.
Figure 17:
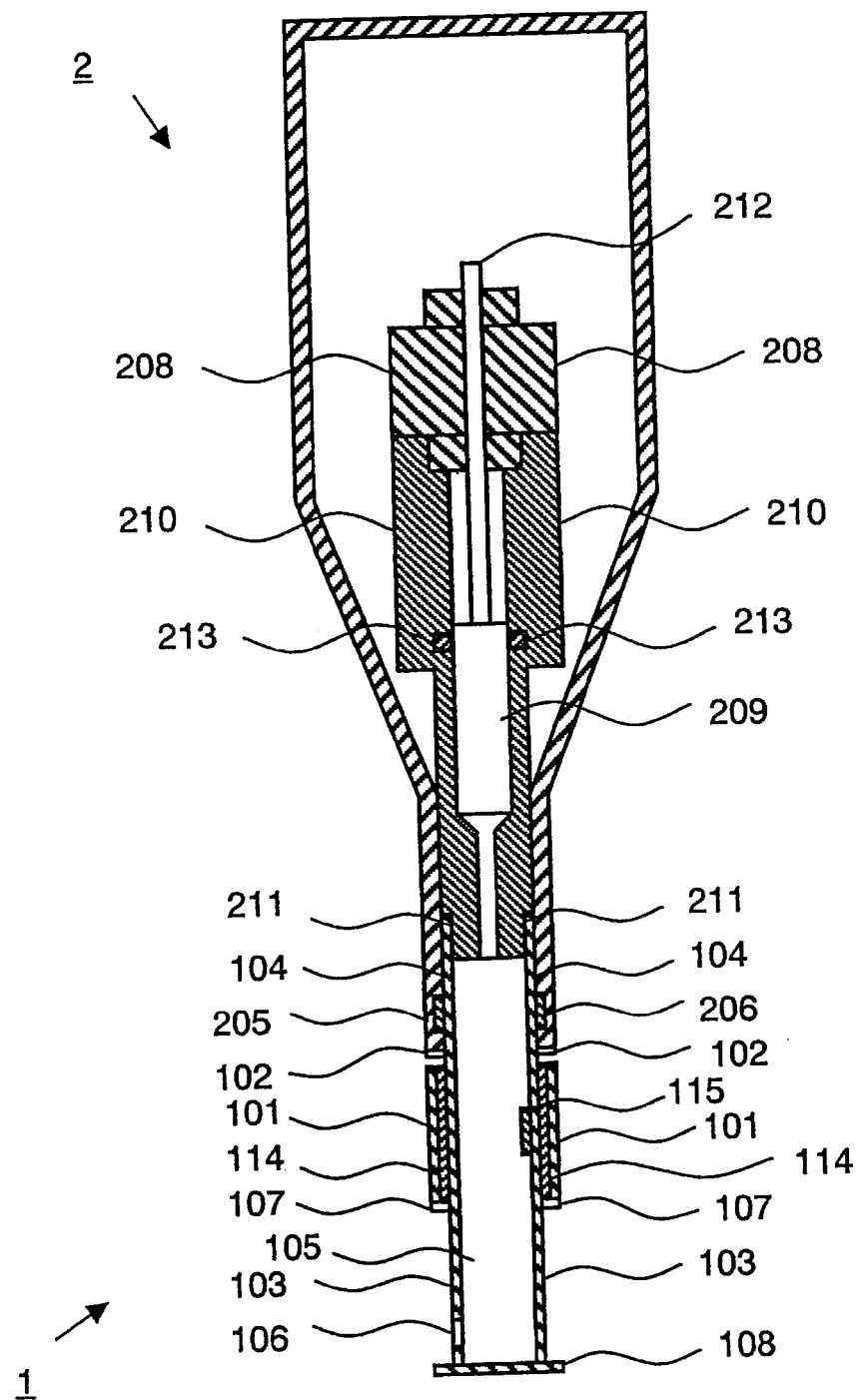
FIG. 17 A diagram for describing another step in the steps for measuring an analyte in a sample by using a measurement cell 1 and a measurement device 2 of the present invention.

First, the measurement cell 1 is moved in the direction of arrow Y so that the measurement cell attach-detach portion 211 of the measurement device 2 and the suction opening 113 of the measurement cell 1 are connected, thereby attaching the measurement cell 1 to the measurement device 2 through the measurement cell attaching portion 201 (FIG. 16). The opening part of the measurement cell attaching portion 201 has a size that allows insertion of the measurement cell main body 103 but disallows insertion of the protection cover 101. Thus, the protection cover 101 that was held by the first protection-cover-holding part 102 is not inserted into the opening part of the measurement cell attaching portion 201, and as the main body 103 is inserted into the opening part of the measurement cell attaching portion 201, the protection cover 101 moves in the direction of arrow Z along the main body 103, so as to expose the optical window portion 104 in the measurement device 2. Since the measurement cell main body 103 is provided with the second protection-cover-holding part 107, the protection cover 101 does not move to pass over the second protection-cover-holding part 107 (FIG. 17).

Figure 19:
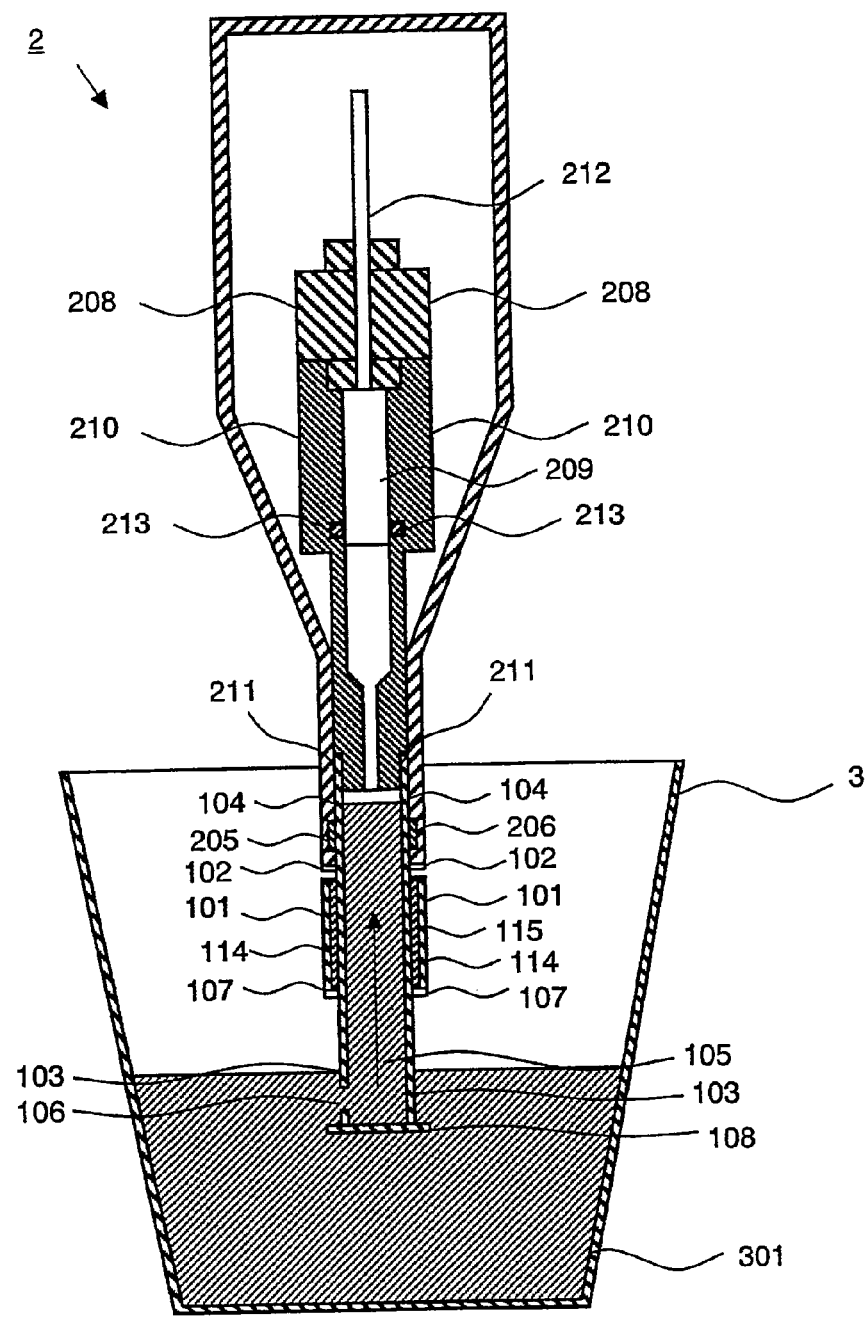
FIG. 19 A diagram for describing still another step in the steps for measuring an analyte in a sample by using a measurement cell 1 and a measurement device 2 of the present invention.

Then, into a urine 301 discharged in a paper cup 3, at least the opening part 106 of the measurement cell 1 is immersed (FIG. 18). By pressing the sample supply button 202 under such conditions, CPU 401 allows the suction mechanism 403 to operate. To be specific, the motor 208 in the measurement device 2 is driven to pull up the plunger 209 inside the cylinder 210 through the plunger joint 212, so as to supply a predetermined amount of the urine 301 (for example, 6 mL) from the opening part 106 of the measurement cell 1 to the sample holding part 105 (FIG. 19).

By keeping the plunger 209 at such a position, the urine is kept in the sample holding part 105, not leaking from the opening part 106 or being sucked into the cylinder 210. Upon suspension of the motor 208 and ending of the suction operation by the suction mechanism 403, CPU 401 allows the display portion 207 to show the message notifying the end of the supplying of the sample to the sample holding part 105, and allows the timer, i.e., the timer unit 404, to start to time. After the end of the supplying of the sample, the opening part 106 may be pulled up from the urine 301.

The urine supplied in the sample holding part 105 dissolves the dried reagent carried at the reagent-holding part 115, i.e., anti-human albumin antibody, and an immune reaction between the antigen in the urine, i.e., human albumin, and the anti-human albumin antibody advances.

Then, when the CPU 401 determines that a predetermined time (for example, two minutes) has elapsed from the completion of the sample supply into the sample holding part 105 based on the signal from the timer unit 404, the CPU 401 allows the light source 205 to carry out light application.

A laser beam outputted from the light source 205 is applied to the urine in the sample holding part 105 through the optical window portion 104: light scattered in the urine and outputted from the optical window portion 104 is received by the optical receiver 206.

The CPU 401 reads out the calibration curve that shows the relationship between the exit light intensity and the human albumin concentration stored in the memory 402, and by referring to the calibration curve, the CPU 401 converts the exit light intensity received by the optical receiver 206 into the human albumin concentration. The obtained human albumin concentration is displayed on the display portion 207. By showing the human albumin on the display portion 207, the user knows the completion of the measurement on the human albumin concentration.

The obtained human albumin concentration is preferably stored in the memory 402 along with the time timed by the timer unit 404.

Figure 20:
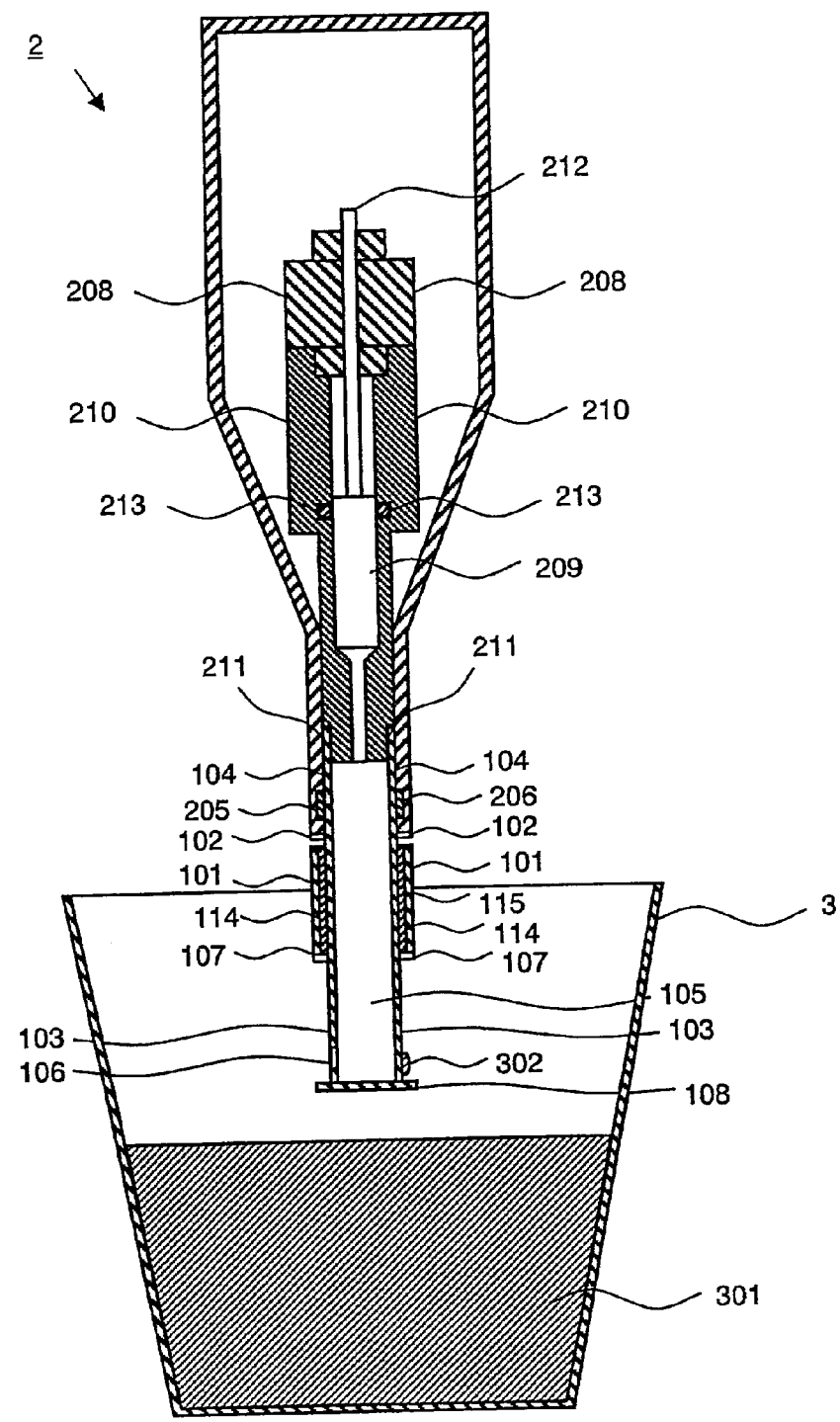
FIG. 20 A diagram for describing still another step in the steps for measuring an analyte in a sample by using a measurement cell 1 and a measurement device 2 of the present invention.

Then, the measurement device 2 with the measurement cell 1 attached or the paper cup 3 is moved so that the opening part 106 of the measurement cell 1 is positioned on top of the paper cup 3. With a pressing of the sample discharge button 203 under such a condition, the motor 208 is driven to push down the plunger 209 inside the cylinder 210 through the plunger joint 212, to discharge the urine in the sample holding part 105 into the paper cup 3 (FIG. 20). The paper cup 3 was drained of the discharged urine 301, and the paper cup 3 itself is discarded.

Figure 21:
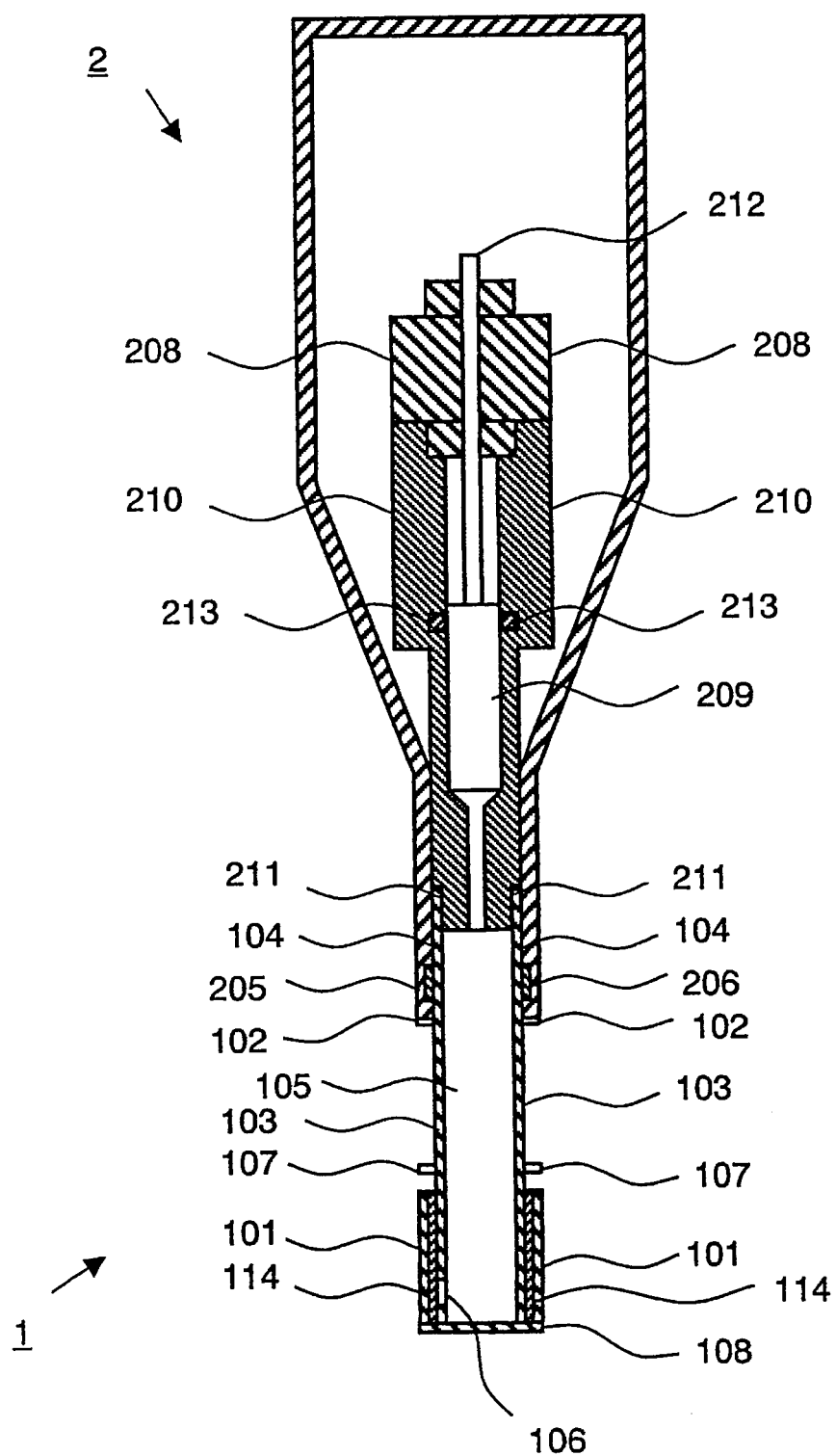
FIG. 21 A diagram for describing still another step in the steps for measuring an analyte in a sample by using a measurement cell 1 and a measurement device 2 of the present invention.

Then, the protection cover 101 of the measurement cell 1 is moved in the direction of the opening part 106 along the measurement cell main body 103. Since the measurement cell main body 103 is provided with the third protection-cover-holding part 108, the protection cover 101 stays at the position of the third protection-cover-holding part 108, and is kept with the opening part 106 covered (FIG. 21). By doing this, the urine 302 attached to the outer surface of the measurement cell 1 between the second protection-cover-holding part 107 and the third protection-cover-holding part 108 (ref. FIG. 20) can be wiped off with a polymer absorbent sheet, i.e., the absorbent 114 disposed inside the protection cover 101.

Figure 22:
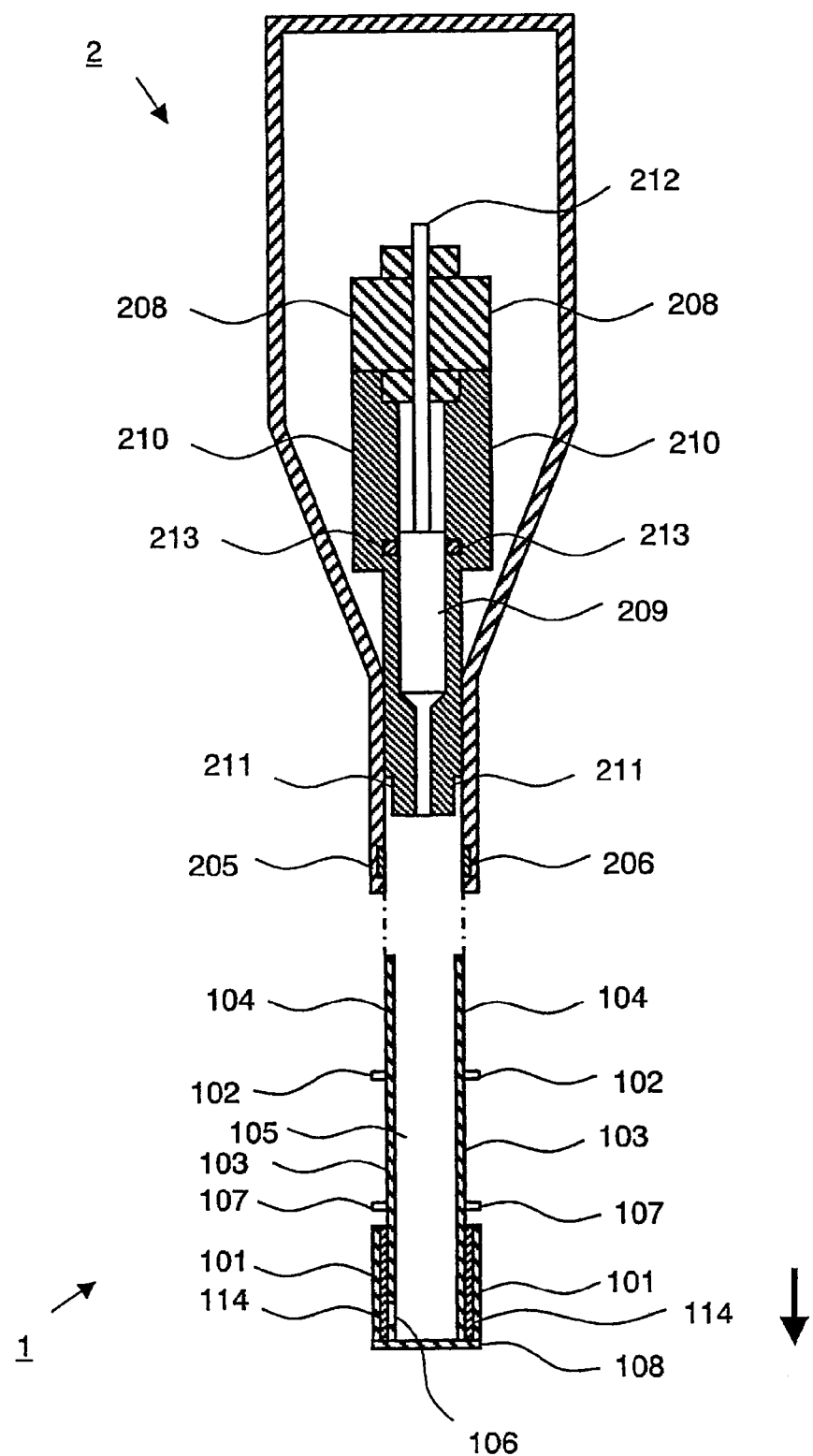
FIG. 22 A diagram for describing still another step in the steps for measuring an analyte in a sample by using a measurement cell 1 and a measurement device 2 of the present invention.

Lastly, the measurement cell 1 is pulled out from the measurement device 2 while holding the protection cover 101 (FIG. 22). By doing this, hands can be prevented from being contaminated by mistakenly touching the sample attached to the measurement cell 1 when the user is removing the measurement cell 1 from the measurement device 2.

Further, the obtained human albumin concentration can be recorded in a storage medium such as an SD card by the recording unit 405. By storing the record in a removable storage medium, the measurement result can be taken out from the measurement device 2 easily, and therefore the storage medium can be brought or sent to an analysis expert to ask for analysis.

Further, the obtained human albumin concentration can be sent out of the measurement device 2 by a transmission unit 406. By doing this, the measurement result can be sent to an analysis-related section in a hospital or to an analysis-related institute, and can be analyzed by them, and therefore the time from the measurement to the analysis can be reduced.

Further, a receiving unit 407 for receiving the analysis result from the analysis-related section in a hospital or an analysis-related institute is provided. By doing this, feedback about the analysis result can be given to the user quickly.

Although the plunger 209 in the cylinder 210 is operated through the motor 208 of the linear-type step motor as the suction mechanism 403 in the above embodiments, the configuration is not limited thereto. A step motor other than the linear-type, and a direct current motor may also be used. The suction mechanism may also be manual.

Although the urine is taken in the paper cup in the above embodiments, without limitation, a transportable container such as a plastic cup, or a urine container provided in a toilet bowl may also be used.

Although the message for notifying the completion of the sample supply into the sample holding part 105 is shown on the display portion 207 in the above embodiment, the notification may also be done by a sound such as a buzzer instead.

INDUSTRIAL APPLICABILITY

Based on the measurement cell of the present invention, since the optical window is protected when not in measurement without being exposed and measurement error based on the dirt and damage on the optical window portion can be prevented, it is useful in analysis and testing field.

The invention claimed is:

1. A measurement cell comprising:
    a sample holding part for holding a sample;
    an opening part for supplying the sample to an inner portion of said sample holding part;
    an optical window portion for allowing light to enter said sample holding part, and allowing light to exit said sample holding part;
    a protection cover for protecting said optical window portion, provided movably along the circumference of said sample holding part; and
    a first protection-cover-holding part for holding said protection cover at a position where said optical window portion is covered with said protection cover.

2. The measurement cell in accordance with claim 1, further comprising a second protection-cover-holding part for holding said protection cover at the position where said optical window portion and said opening part are being exposed.

3. The measurement cell in accordance with claim 1, further comprising a third protection-cover-holding part for holding said protection cover at the position where said opening part is being covered with said protection cover.

4. The measurement cell in accordance with claim 1, further comprising an absorbent disposed inside said protection cover.

5. The measurement cell in accordance with claim 2, further comprising an absorbent disposed inside said protection cover.

6. The measurement cell in accordance with claim 3, further comprising an absorbent disposed inside said protection cover.

* * * * *